(12) United States Patent
Ni et al.

(10) Patent No.: US 11,674,957 B2
(45) Date of Patent: Jun. 13, 2023

(54) MOLECULAR WIRES FOR DETECTING A BIOLOGICAL OR CHEMICAL ENTITY OR EVENT

(71) Applicant: VELANIDI TECHNOLOGIES LLC, Portland, OR (US)

(72) Inventors: Jane Ni, Portland, OR (US); David Shykind, Buxton, OR (US); Devin Wiley, Hillsboro, OR (US)

(73) Assignee: VELANIDI TECHNOLOGIES LLC, Portland, OR (US)

(*) Notice: Subject to any disclaimer, the term of this patent is extended or adjusted under 35 U.S.C. 154(b) by 0 days.

(21) Appl. No.: 17/245,118

(22) Filed: Apr. 30, 2021

(65) Prior Publication Data

US 2021/0341473 A1 Nov. 4, 2021

Related U.S. Application Data

(60) Provisional application No. 63/017,981, filed on Apr. 30, 2020.

(51) Int. Cl.
*G01N 33/543* (2006.01)
*C12Q 1/6816* (2018.01)
*C12Q 1/6804* (2018.01)

(52) U.S. Cl.
CPC ..... *G01N 33/54373* (2013.01); *C12Q 1/6804* (2013.01)

(58) Field of Classification Search
None
See application file for complete search history.

(56) References Cited

U.S. PATENT DOCUMENTS

2005/0048651 A1 3/2005 Ryttsen et al.
2008/0047926 A1 2/2008 Santini et al.
(Continued)

FOREIGN PATENT DOCUMENTS

WO WO-2021222674 A1 * 11/2021 ........... C12Q 1/6804

OTHER PUBLICATIONS

Agard et al., A strain-promoted [3 + 2] azide-alkyne cycloaddition for covalent modification of biomolecules in living systems, J. Am. Chem. Soc., 126(46):15046-7 (2004).
(Continued)

*Primary Examiner* — Robert T. Crow
(74) *Attorney, Agent, or Firm* — Marshall, Gerstein & Borun LLP

(57) ABSTRACT

Enantiomeric pairs of molecular wires comprised of oligomeric nucleic acids, wherein the oligomers of each wire possess identical nucleobase pair sequences and thus identical conductivity as between wires, are constructed and used to sense biological or chemical entities of interest at the cellular or molecular level. The oligomeric molecular wires conduct voltage inputs to sensing subsystem integrated circuitry, either from an electrostatic potential arising from a targeting agent (i.e., a capture agent) binding to an intended biological or chemical target molecule, or from an electrostatic potential associated with a reference molecule that has non-specific interactions with the environment. The chirality of the oligomers imparts selectivity to either the targeting agent or the reference molecule during assembly of the sensing subsystem.

37 Claims, 15 Drawing Sheets

(56) References Cited

U.S. PATENT DOCUMENTS

| | | | | |
|---|---|---|---|---|
| 2010/0062436 | A1* | 3/2010 | Jarosch | C12Q 1/6816 435/6.14 |
| 2011/0230736 | A1 | 9/2011 | Tepper et al. | |
| 2015/0168337 | A1 | 6/2015 | Soleymani et al. | |
| 2017/0306284 | A1 | 10/2017 | Yamanishi et al. | |
| 2017/0356030 | A1* | 12/2017 | Boyanov | C12Q 1/6818 |
| 2019/0090801 | A1 | 3/2019 | Rogers et al. | |
| 2020/0319165 | A1 | 10/2020 | Shykind et al. | |

OTHER PUBLICATIONS

Aragonès et al., Measuring the Spin-Polarization Power of a Single Chiral Molecule, Small, 13:1602519-24 (2017).
Arnold et al., DNA charge transport: from chemical principles to the cell, Cell Chem. Biol., 23:183-197 (2016).
Beall et al., Effects of the Backbone and Chemical Linker on the Molecular Conductance of Nucleic Acid Duplexes, J. Am. Chem. Soc., 139:6726-35 (2017).
Beratan, Why are DNA and Protein Electron Transfer So Different?, Annu. Rev. Phys. Chem. 70, 71-97 (2019).
Chan et al., Polytriazoles as copper(I)-stabilizing ligands in catalysis, Org. Lett., 6(17):2853-5 (2004).
Dien et al., Progress Toward a Semi-Synthetic Organism with an Unrestricted Expanded Genetic Alphabet, J. Am. Chem. Soc., 140:16115-16123 (2018).
Fantoni et al., A hitchhiker's guide to click-chemistry with nucleic acids, Chem. Rev., 121(12):7122-54 (2021).
Furuhata et al., Highly Conductive Nucleotide Analogue Facilitates Base-Calling in Quantum-Tunneling-Based DNA Sequencing, ACS Nano 13, 5028-35 (2019).
Genereux et al., Mechanisms for DNA charge transport. Chem. Rev. 110:1642-62 (2010).
Hauser et al., Utilising the left-helical conformation of L-DNA for analysing different marker types on a single universal microarray platform, Nucleic Acids Res., 34(18):5101-11 (2006).
Hoshika et al., Hachimoji DNA and RNA: A genetic system with eight building blocks, Science, 363(6429):884-7 (2019).
Hueberger et al., An Alternative Nucleobase Code: Characterization of Purine-Purine DNA Double Helices Bearing Guanine-Isoguanine and Diaminopurine 7-Deaza-Xanthine Base Pairs. ChemBioChem, 9:2779-2783 (2008).
International Aplication No. PCT/US2021/030038, International Search Report and Written Opinion, dated Sep. 9, 2021.
International Application No. PCT/US20/26923, International Search Report and Written Opinion, dated Sep. 4, 2020.
Kawai et al., Hole transfer in LNA and 5-Me-2'-deoxyzebularine-modified DNA, J. Am. Chem. Soc., 134(22):9406-9 (2012).
Kawai et al., Hole Transfer Kinetics of DNA. Acc. Chem. Res. 46, 2616-25 (2013).
Kawai et al., HOMO Energy Gap Dependence of Hole-Transfer Kinetics in DNA, J. Am. Chem. Soc., 134:4806-11 (2012).
Kawai et al., Long-Range Charge Transfer through DNA by Replacing Adenine with Diaminopurine. J. Am. Chem. Soc. 132:627-30 (2010).
Kiran et al., Helicenes—A New Class of Organic Spin Filter. Adv. Mater., 28:1957-62 (2016).
Kolb et al., Click Chemistry: Diverse chemical function from a few good reactions, Angew Chem Int. Ed., 40:2004-21 (2001).
Kolb et al., The growing impact of click chemistry on drug discovery, DDT, 8(24):1128-37 (2003).
Lewis et al., Click chemistry in situ: acetylcholinesterase as a reaction vessel for the selective assembly of a femtomolar inhibitor from an array of building blocks, Angew Chem Int Ed Engl., 41(6):1053-7 (2002).
Li et al., Natural-like Replication of an Unnatural Base Pair for the Expansion of the Genetic Alphabet and Biotechnology Applications. J. Am. Chem. Soc. 136, 826-829 (2014).
Liu et al., Size-Expanded Analogues of dG and dC: Synthesis and Pairing Properties in DNA. J. Org. Chem. 70, 639-647 (2005).
Liu et al., Toward a New Genetic System with Expanded Dimensions: Size-Expanded Analogues of Deoxyadenosine and Thymidine. J. Am. Chem. Soc. 126, 1102-1109 (2004).
Manetsch et al., In situ click chemistry: Enzyme inhibitors made to their own specifications, J Am Chem Soc., 126:12809-18 (2004).
Nakatani et al., Modulation of DNA-Mediated Hole-Transport Efficiency by Changing Superexchange Electronic Interaction. J. Am. Chem. Soc. 122, 5893-5894 (2000).
Rostovtsev et al., A stepwise huisgen cycloaddition process: copper(l)-catalyzed regioselective "ligation" of azides and terminal alkynes, Angew Chem Int Ed Engl., 41(14):2596-9 (2002).
Speers et al., Activity-based protein profiling in vivo using a copper(i)-catalyzed azide-alkyne [3 + 2] cycloaddition, J. Am. Chem. Soc., 125(16):4686-7 (2003).
Tang et al., DNA-directed assembly of protein microarrays, Frontiers in Bioscience, 13(13):5755-71 (2008).
Tornøe et al., Peptidotriazoles on solid phase: [1,2,3]-triazoles by regiospecific copper(i)-catalyzed 1,3-dipolar cycloadditions of terminal alkynes to azides, J. Org. Chem., 67(9):3057-64 (2002).
Waser et al., Cobalt-catalyzed hydroazidation of olefins: convenient access to alkyl azides, J. Am. Chem. Soc., 127(23):8294-5 (2005).
Wierzbinski et al., Effect of Backbone Flexibility on Charge Transfer Rates in Peptide Nucleic Acid Duplexes. J. Am. Chem. Soc. 134, 9335-9342 (2012).
Winnacker et al., Artificial genetic sets composed of size-expanded base pairs, Angew. Chem. Int. Ed., 52:12498-508 (2013).
Young et al., Mirror-image oligonucleotides: history and emerging applications, Chem. Eur. J., 25:7981-90 (2019).
Zhang et al., Ruthenium-catalyzed cycloaddition of alkynes and organic azides, J Am Chem Soc., 127:15998-9 (2005).
Zhu et al., Switchable DNA wire: deposition-stripping of copper nanoclusters as an "On-Off" nanoswitch, Scientific Reports, 6(1):19515 (2016).

* cited by examiner

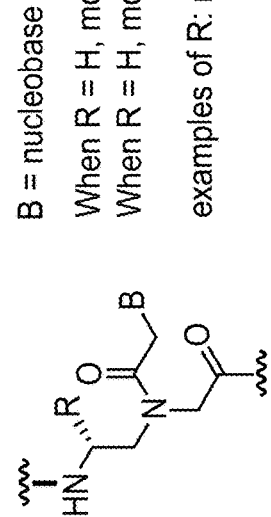
PNA backbone motif
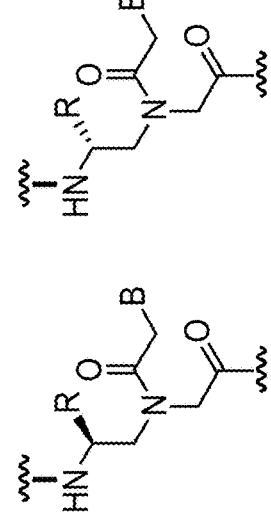
FIG. 5
B = nucleobase
When R = H, monomer is achiral (aminoethylglycine motif, aeg)
When R ≠ H, monomer is chiral (γ-modified PNA)
examples of R: natural amino acid side chains, polyethylene glycol
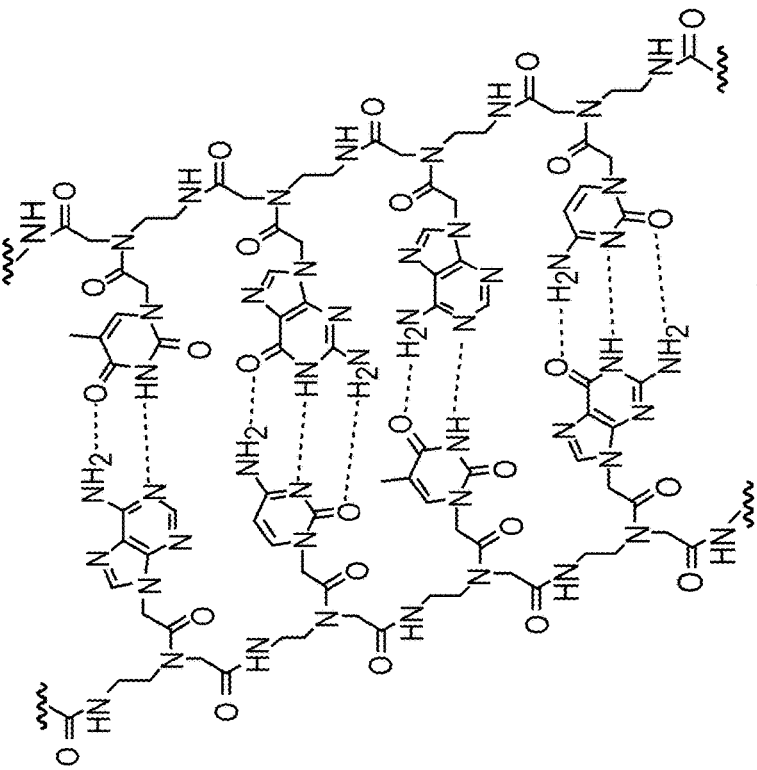
FIG. 7
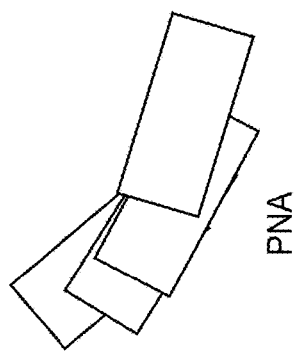
PNA
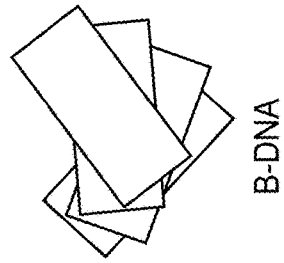
B-DNA
FIG. 6

PNA-DNA aeg-PNA monomer

*right-handed*  *left-handed*

Duplexes composed entirely of achiral aeg-PNA do not have a preferred handedness.

A chiral seed will induce a preferred handedness.

Canonical nucleobases
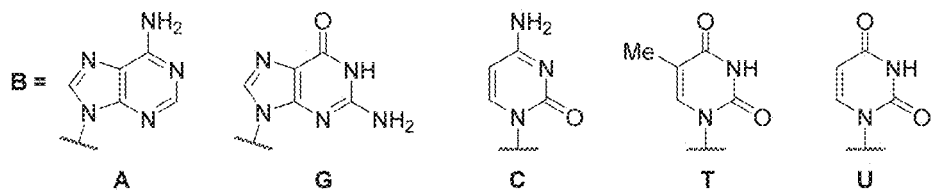
Non-canonical nucleobases
*size-expanded analogues*
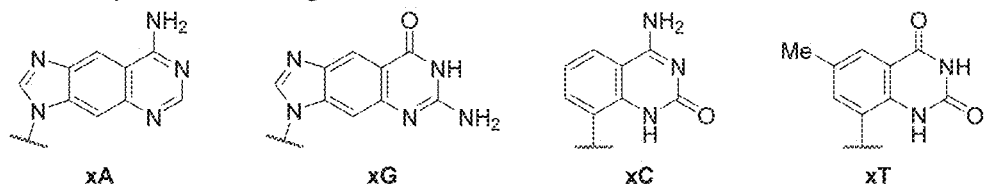
*deaza analogues*
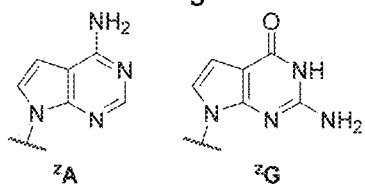
*hydrophobic analogues*
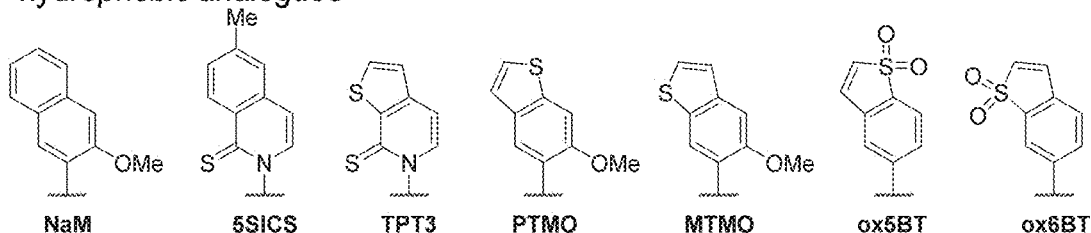
*hachimoji analogues*
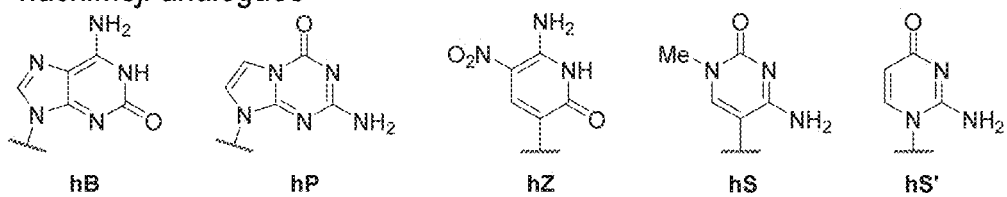
*additional purine analogues*
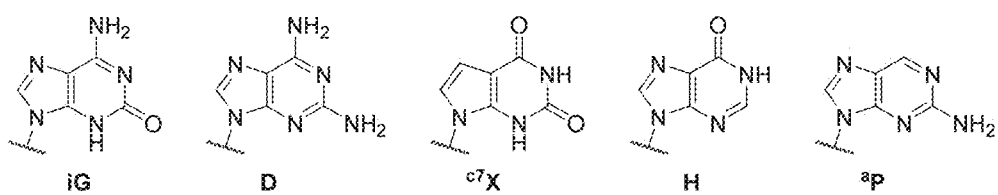
*additional pyrimidine analogues*
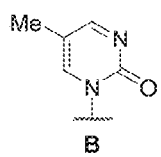
FIG. 10

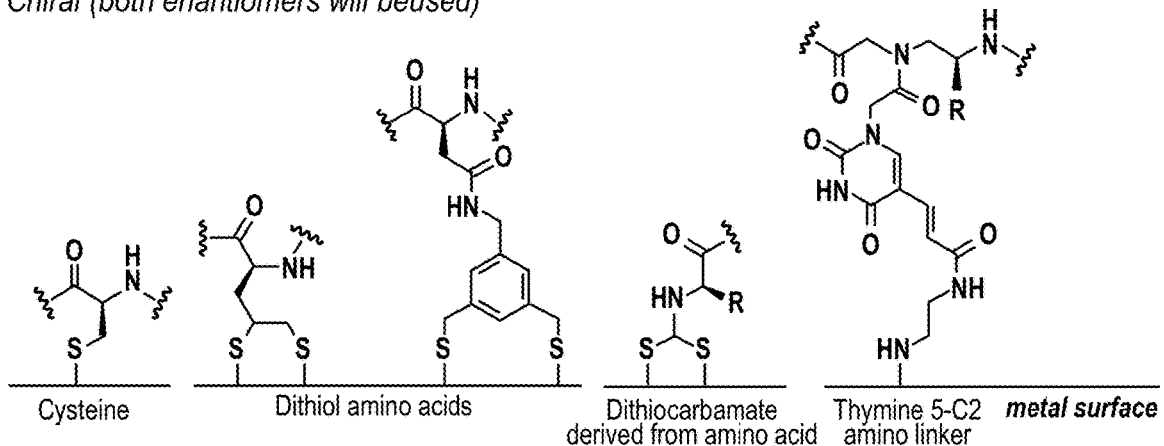
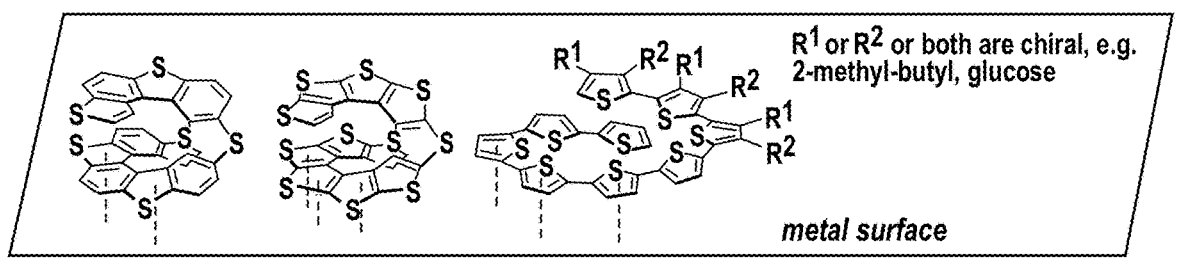
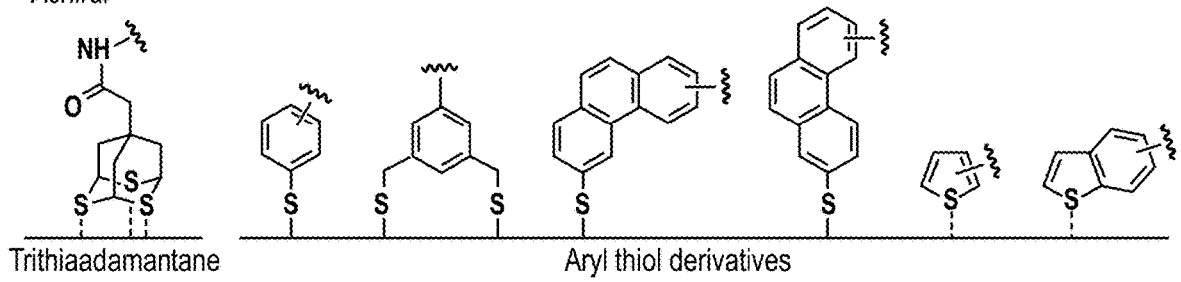
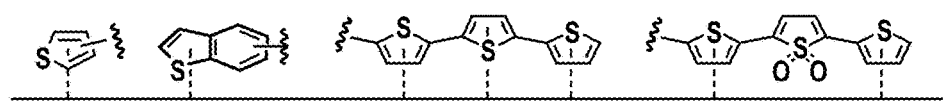
FIG. 12

PNA conjugation to antigen binding component

*Total synthesis via solid phase peptide synthesis*

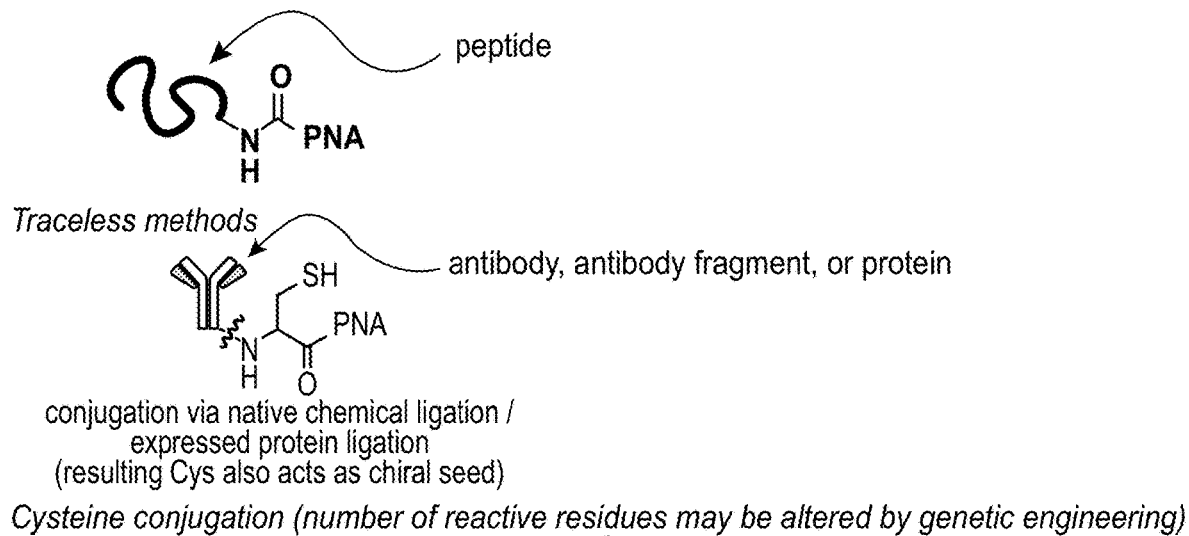

*Traceless methods* conjugation via native chemical ligation /
expressed protein ligation
(resulting Cys also acts as chiral seed)

*Cysteine conjugation (number of reactive residues may be altered by genetic engineering)*

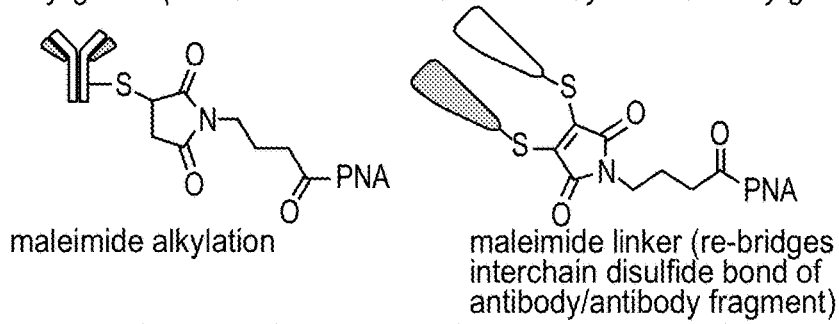

maleimide alkylation maleimide linker (re-bridges
interchain disulfide bond of
antibody/antibody fragment)

*Lysine conjugation (number of reactive residues may be altered by genetic engineering)*

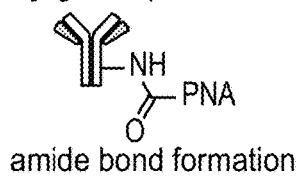

amide bond formation

*Non-natural amino acid incorporation and subsequent conjugation*

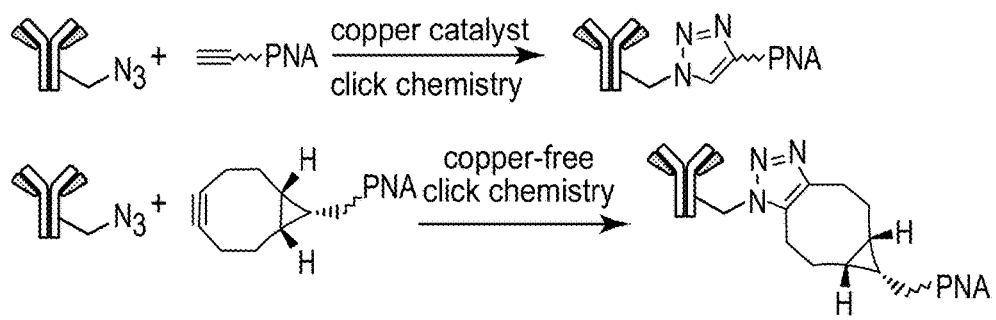

FIG. 14

MOLECULAR WIRES FOR DETECTING A BIOLOGICAL OR CHEMICAL ENTITY OR EVENT

CROSS-REFERENCE TO RELATED APPLICATIONS

This application claims the benefit of U.S. Provisional Patent Application No. 63/017,981, filed on Apr. 30, 2020, the entirety of which is hereby incorporated herein by reference.

FIELD OF THE DISCLOSURE

The present disclosure relates to the use of chiral molecular wires to transport electrical charge or an electrical signal.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Prior research has studied the charge transport characteristics of DNA with the goal of applying this technology towards next generation integrated circuits. Beratan et al. have discovered that replacing the sugar phosphate backbone of DNA with a peptide backbone yields significant increases in conductivity. Many researchers have synthesized noncanonical nucleobases for a variety of purposes, including increasing the information storage capacity of DNA/RNA, studying the mechanism of DNA charge transfer, and facilitating DNA sequencing. Work by Nielsen, Zhao, and others, have demonstrated the high stability of polyamide-backbones that are associated with PNA-PNA and PNA-DNA duplexes (in comparison to DNA-DNA duplexes). The thermal stability results from the lack of electrostatic repulsion between PNA-DNA and PNA-PNA strands, combined with the flexibility of the polyamide backbone. The relative inability of proteases and nucleases to identify the polyamide backbone of PNA further increases the lifetime of these molecules both in vitro and in vivo biological systems. Chiral, organic molecular wires (helicenes and α-helical peptides, respectively) have been studied and showed that, in the absence of a ferromagnetic spin filter, enantiomeric wires do not differ in conductivity. See Kiran et al., Adv. Mater. 28, 1957-1962 (2016) and Medina et al., Small 13, 1602519-1602524 (2017).

SUMMARY

In a system and method for detecting biological or chemical entities of interest, a small difference between two voltage inputs is amplified. The first input comes from an electrostatic potential arising from a capture agent (also referred to herein as "targeting agent" or "target agent" or "target binding molecule") when bound to an intended chemical or biological target molecule, such as an antigen or other disease-associated cell marker. The second input is from an electrostatic potential associated with a reference molecule (also referred to herein as "reference compound") that has non-specific interactions with the environment. Both the capture agent and reference molecule are electrically connected to the integrated circuitry of the system via molecular wires. Any conductivity difference in the molecular wires can produce a differential mismatch signal that is unrelated to a specific chemical or biological binding event, such an antigen binding event. This voltage difference lowers the dynamic range of the differential comparator and reduces the specificity and sensitivity of the system. The system may be a device or apparatus such as the micro/nano-sensing-deciding-effecting-device (MNSDED) disclosed in U.S. Patent Publication No. 2020/0319165, for example. The entire disclosure of U.S. Patent Publication No. 2020/0319165 is hereby incorporated herein by reference.

The present disclosure describes a method and system through which chiral oligomeric nucleic acids can function as molecular wires, wherein these oligomers possess identical nucleobase pair sequences and thus identical conductivity. The chirality of these oligomers imparts selectivity to either the capture agent or the reference molecule (i.e., reference compound) of the system, enabling the site-specific localization of the capture agent and reference molecule upon a surface. The present disclosure more specifically provides chemistry that allows for chiral DNA, peptide nucleic acids (PNAs), G-quadruplexes, I-Motifs, Triplex Formations, or other non-canonical DNA structure formations. These non-canonical nucleic acid structure formations provide significant benefits for in vivo applications. For example, PNAs enable more stability when administered to an in vivo system because they have a large binding strength to complementary PNAs or DNAs (when compared to DNA-DNA homoduplexes), they have higher selectivity against base pair mismatches, and they avoid degradation by proteases and nucleases. The present disclosure further describes a system incorporating and method of using non-canonical nucleobases, which allow for expansion of the nucleic acid code that may be used and the ability to further optimize conductivity and annealing temperatures between complementary oligomer pairs. The present disclosure further describes specific chemistry that enables charge transfer from the oligomeric wires to the integrated circuitry of the system—chemistry that bypasses Debye shielding within physiologic environments. As described herein, the oligomeric molecular wires are disclosed such that they have optimal annealing temperatures for system design, minimal size, maximal conductivity, high stability in physiologic solution, resistance to oxidative degradation and the ability to evade degrading enzymes including proteases and nucleases.

The following disclosure describes a system and method of a sensing subsystem required for detecting biological or chemical entities of interest. This sensing system and method include key components that enable the "sensing subsystem" component of a MNSDED or other system.

The embodiments of the present disclosure include the use of pairs of chiral oligomeric molecular wires in the form of multiplexes. The pair comprises two molecular wires that are enantiomers. For example, each oligomeric wire may be a duplex comprising two complementary sequences of monomers arranged in stereochemically-defined helical structures. One molecular wire of each pair, possessing a defined absolute configuration, is capable of transporting electrical charge or an electrical signal from an attached capture agent to integrated circuitry of any suitable sensing or diagnostic device (e.g., the integrated circuitry of a MNSDED) through, for an example, an electrically-conductive pad. The other molecular wire of each pair, possessing opposite absolute configuration, transports electrical charge or an electrical signal from a reference molecule (i.e., reference compound) to the integrated circuitry. An oligomeric molecular wire may transfer electrical information, including electrical current or potential that is associated with a specific binding event, such as a capture agent binding to its associated target. In one embodiment, one or more molecular wires may enable a MNSDED or other device to differentiate between pathogenic entities of interest and non-pathogenic entities. In other embodiments, one or more molecular wires may enable a MNSDED or other device to identify the presence of any chemical or biological compound (or entity) of interest.

Specifically, this sensing subsystem may employ oligomeric peptide nucleic acids (PNAs) as a molecular wire. Additional molecular wire structures are described, including various arrangements of two or more strands of nucleic acids (including but not limited to G-quadruplexes, I-motifs, triplex formations, paranemic crossover DNA, double crossover DNA and others) as well as structures with non-canonical backbones (including but not limited to morpholino and locked nucleic acids). Paranemic crossover DNA is highly resistant to nucleases compared to double-stranded DNA. PNAs are also not substrates of proteases and nucleases, thus enabling higher stability in physiologic solutions. PNAs exhibit a large binding strength to complementary PNAs or DNAs, allowing for high stability between complementary sequences with fewer nucleobase pairs.

The PNAs may be attached to the integrated circuitry of the MNSDED or other device through specific chemistry that bypasses Debye shielding within physiologic environments. Extending the pi-system of the nucleobases by pi-stacking or conjugation via an unsaturated conductive functional handle to the conductive pad creates a path that is more conductive than the solution. Additionally, placing the nucleobases of the molecular wire in close proximity (i.e., <2 nm) to the associated conductive pad (e.g., environmental-electronic binding interface pad or "EEBIP") of the device may also enhance conductivity.

While the most basic PNA backbone, based on the amino acid glycine, is achiral and does not favor one helical handedness over the other, addition of one or more chiral monomers stabilizes one enantiomer and forces the helix to adopt a specific absolute configuration. Chiral PNAs facilitate attachment of a capture agent to the desired conductive pads (EEBIPs) among several pads, with one enantiomer used for the targeting pad, and the opposite enantiomer used for the reference pad. This stereospecificity of PNA hybridization allows for identical nucleobase sequences, with identical conductivity, to be associated with pads, while still distinguishing between target and reference pads.

In one embodiment of the present disclosure, chirality is used as a recognition element in synthesizing helical molecular wires to enable efficient manufacturing of antigen detecting apparatuses and systems, such as a MNSDED sensing subsystem.

In another embodiment of the present disclosure, conductivity of the molecular wire which carries the electrical signal generated by, for example, an antigen binding event, is improved by substituting noncanonical nucleobases in for naturally occurring nucleobases. Employing noncanonical nucleobases can enable tuning of the duplex annealing temperature and optimization of conductivity, and can provide additional protection against enzymatic degradation. The desired annealing temperature is greater than physiologic temperature and less than any temperature that would denature, degrade, or otherwise damage a targeting agent.

In yet another embodiment of the present disclosure, one of the strands of the molecular wire is modified such that the terminus has a heterocyclic molecule capable of dative bonding to a gold or other metallic surface with maximal pi bonding overlap between the metal and the adjacent nucleobases in the DNA wire, ensuring maximum conductivity along the entire path from a metal pad to a target binding molecule (i.e., capture agent) or from a metal pad to a reference molecule (i.e., reference compound).

BRIEF DESCRIPTION OF THE DRAWINGS

FIG. 5 shows an exemplary peptide nucleic acid (PNA) monomer structure.

FIG. 6 shows an arrangement of nucleobase pairs in helical stacks in B-DNA and PNA, viewed along the helical axis.

FIG. 7 shows an exemplary structure of a PNA-PNA homoduplex.

FIG. 10 shows exemplary nucleobases for nucleic acid molecular wires.

FIG. 12 shows exemplary conductive functional handles that may be used to form the metallic EEBIP surface-PNA wire connection.

FIG. 14 illustrates exemplary methods for conjugating the PNA molecular wire to an antigen binding component.

DETAILED DESCRIPTION OF THE DRAWINGS

Electrical detection of a chemical or biological binding event, such as an antibody binding event, is essentially a differential voltage measurement. As disclosed in U.S. Patent Publication No. 2020/0319165, for example, detecting antigen binding by a MNSDED requires amplifying and detecting small potential changes which arise from the dielectric constant differences between a target binding molecule (i.e., a capture agent) that has bound a target ligand (or other target entity) and a reference molecule (i.e., reference compound). Both target-binding and reference molecules are covalently attached to conductive surfaces such as pads. The pads or other conductive surfaces are in turn electrically connected to the input terminals of a differential amplifier/latch (a sense amplifier), which amplifies and detects the binding differential voltage. Any difference in conductivity in the two paths can produce a differential signal that is unrelated to the binding event (e.g., an antigen binding event), thus lowering the sensitivity to an actual target-binding to antigen event. Further, the absolute conductivity of both paths should be as large as possible (within design constraints for the MNSDED or other device) to minimize solution Debye and common-mode voltage(s) effects.

As described herein, a chiral oligonucleotide multiplex, such as double-stranded DNA, may be used as a molecular wire to transmit binding information (e.g., on a MNSDED). The specific pairing of complementary purine and pyrimidine bases provides the additional benefit of facilitating efficient, site-specific installation of both the sensing component (i.e., capture agent) and reference (i.e., reference compound), minimizing the need for protecting groups or masks. However, the conductivity of oligonucleotides, such as DNA, is sequence-dependent, with some sequences conducting poorly. This sensitivity can present a confounding variable if different nucleobase sequences are used for the target and reference charge transfer (electrical signal) paths.

Figure 1:
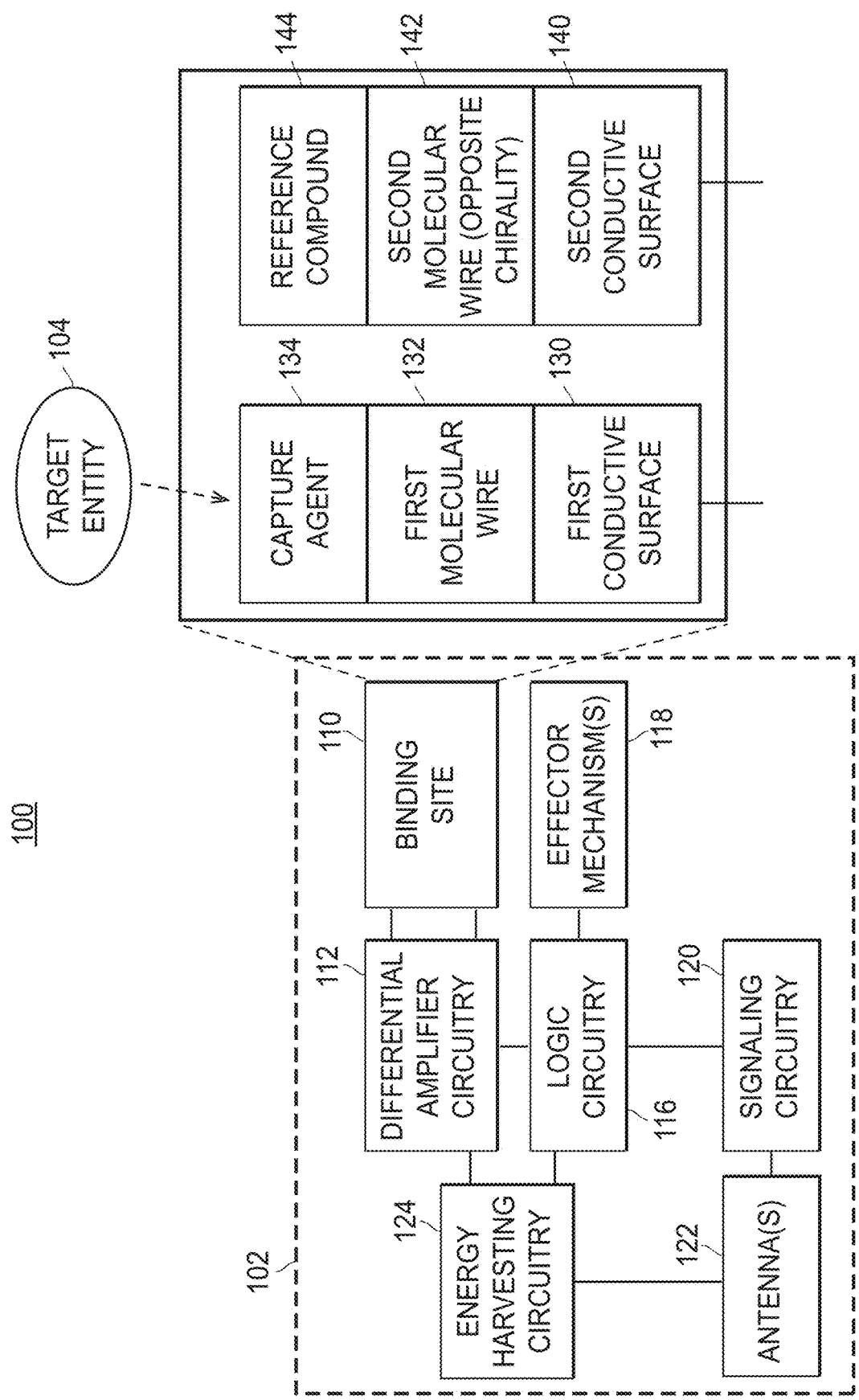
FIG. 1 is a block diagram of an example environment in which a device of this disclosure can detect a biological or chemical entity.

FIG. 1 is a block diagram of an example environment 100 in which a device 102 of this disclosure can detect a target entity 104. The environment 100 may be a physiological environment (in vivo or ex vivo) or a non-physiological environment, depending on the use case, and the target entity 104 may be any biological or chemical entity of interest within the environment 100 (e.g., a particular molecule, chemical, receptor, cell, etc.).

While the device 102 includes nanoscale components as discussed below, the device 102 as a whole may be a nanoscale or microscale device (e.g., a MNSDED as described in U.S. Patent Publication No. 2020/0319165) or a larger-scale device or system. For example, the device 102 may be a MNSDED used in vivo, a MNSDED used ex vivo or in non-physiological environments, or a larger device used ex vivo or in non-physiological environments. For ease of explanation, the following description primarily refers to embodiments in which the device 102 (or a similar device) is a MNSDED.

The example device 102 includes a binding site 110 that is generally configured to attach/bind to target entities of the same type as target entity 104. While FIG. 1 shows only a single binding site 110, the device 102 may include any suitable number (e.g., tens, hundreds, thousands, etc.) of similar binding sites, which may all be configured to attach to the same type of target entity or may include different binding sites configured to attach to different types of target entities. The binding site 110 is discussed in further detail below.

The binding site 110 is electrically coupled to inputs of differential amplifier circuitry 112, which may generally be any circuit capable of amplifying and/or detecting a change in capacitance or voltage across the inputs. For example, the differential amplifier circuitry 112 may be a regenerative sense amplifier incorporating clocked, cross-coupled pairs with precharge, measure, and latch phases. Preferably, the differential amplifier circuitry 112 has a high common mode rejection ratio (CMRR). The output of the differential amplifier circuitry 112 is electrically coupled to logic circuitry 116, which includes transistor-based logic for making decisions based on the differential voltage (e.g., whether a binding event occurred, and possibly also whether to take any resulting action(s) as discussed below, etc.). The logic circuitry 116 may include a latch circuit followed by a number of logic gates, for example, such that the output of the differential amplifier circuitry 112 triggers the latch when the output exceeds a threshold voltage. The logic circuitry 116 may be within a non-conductive housing of the device 102 (as discussed below with reference to FIG. 2A), and/or may be fabricated using 10 nanometer or smaller transistor node technology, for example.

The logic circuitry 116 generally processes the binding event information (as reflected in the signal output by the differential amplifier circuitry 112), and makes one or more decisions based on that information. For example, the logic circuitry 116 may process the binding event information/signal to determine whether the entity is disease-associated (e.g., a disease-associated cell or virus). In some embodiments, the logic circuitry 116 also determines whether the detection of the binding event/entity requires delivery of a therapeutic agent or other treatment, and outputs an appropriate signal to one or more effector mechanisms 118 to effectuate the delivery (i.e., to activate the effector mechanism(s) 118). The effector mechanism(s) 118 may include one or more electroporating needles with driver circuitry and/or one or more therapeutic release modules (e.g., as disclosed in U.S. Patent Publication No. 2020/0319165), for example. In some embodiments, the device 102 does not include the effector mechanism(s) 118.

Alternatively or additionally, the logic circuitry 116 may determine whether the detection of the binding event/entity requires transmission (or, in some embodiments, requires modification of signal already being transmitted), and outputs an appropriate signal to signaling circuitry 120 to effectuate wireless transmission of the appropriate signal. In this manner, the device 102 may communicate information relating to one or more binding events (e.g., whether a binding event occurred or, if the logic circuitry 116 is electrically coupled to multiple binding sites, whether some threshold number of binding events occurred, etc.) to a remote device or system (e.g., in an embodiment where the device 102 is within a person's body, to a receiver that is external to the person's body, or to another device similar to device 102, etc.). The signaling circuitry 120 is electrically coupled to at least one antenna of antenna(s) 122, via which the signaling circuitry 120 transmits the signals to the destination receiver(s). In some embodiments, the signaling circuitry 120 is also, or instead, configured to receive wireless signals from one or more transmitters/sources (e.g., other devices similar to device 102, and/or devices external to the body or other environment of the device 102). The signaling circuitry 120 may include matching circuitry, diplexer/receiver protection circuitry (e.g., if the signaling circuitry 120 shares any antenna(s) with the energy harvesting circuitry 124 discussed below), and/or any other suitable circuitry for transmitting and/or receiving wireless signals, and may communicate using any suitable communication techniques. The signaling circuitry 120 may employ the components and techniques disclosed in U.S. Patent Publication No. 2020/0319165, for example. In some embodiments, the device 102 does not include the signaling circuitry 120.

To power the differential amplifier circuitry 112 and the logic circuitry 116 (and possibly the effector mechanism(s) 118 and/or signaling circuitry 120), the device 102 includes energy harvesting circuitry 124. The energy harvesting circuitry 124 harvests radio frequency ("RF") energy received through one or more of the antenna(s) 122 (which may or may not be shared by the signaling circuitry 120), and rectifies and multiplies to a voltage sufficient to support stable analog and logic circuit biasing and operation. The energy harvesting circuitry 124 may employ the components and energy harvesting techniques disclosed in U.S. Patent Publication No. 2020/0319165, for example. The antenna(s) 122 may include multilayer and/or multi-turn coils (e.g., any of the antenna structures disclosed in U.S. Patent Publication No. 2020/0319165).

In some embodiments (e.g., for certain ex vivo or non-physiological applications), the logic circuitry 116 and/or energy harvesting circuitry 124 may be external to the device 102. For example, the device 102 may include numerous nanoscale binding sites similar to binding site 110, all disposed on a relatively large substrate (e.g., ones or tens of centimeters in width and/or length), with metal traces and/or wires electrically coupling the output of the differential amplifier circuitry 112 to the input of the logic circuitry 116, and/or electrically coupling the energy harvesting circuitry 124 to the appropriate subsystems of the device 102.

FIG. 1 also depicts an expanded view of the binding site 110. The inputs to the differential amplifier circuitry 112 are electrically coupled to respective conductive (e.g., metal) pads. In particular, one input to the differential amplifier circuitry 112 is electrically coupled to a first conductive surface (e.g., pad) 130, while the other input is electrically coupled to a second conductive surface (e.g., pad) 140. The first conductive surface 130 is electrically coupled to a capture agent 134 through a first molecular wire 132. The second conductive surface 140 is electrically coupled to a reference compound 144 through a second molecular wire 142. While the embodiment descriptions contained herein primarily refer to molecular wires being coupled to conductive "pads," such as the metal pads of lithographically-formed circuits, it is understood that the embodiments disclosed herein may more generally include molecular wires coupled to other suitable types of conductive surfaces.

The first molecular wire 132 and the second molecular wire 142 are composed of chiral oligonucleotide multiplexes (e.g., duplexes) having identical nucleobase sequences and opposite chirality (i.e., absolute configuration). Accordingly, the first and second molecular wires 132, 142 are enantiomers having identical conductivity but orthogonal selectivity in hybridization. The capture agent 134 comprises a chemical or biological compound, such as an antibody, that can interact with (e.g., bind to) the target entity 104. The target entity 104 is a chemical or biological entity that can interact with (e.g., bind to) the capture agent 134. For example, when the capture agent 134 is an antibody, the target entity can be an antigen. The reference compound 144 exhibits non-specific interactions with the environment. The binding of the capture agent 134 to the target entity 104 results in a capacitance different than the capacitance generated by the non-specific interactions the reference compound 144 exhibits with the environment. The first conductive surface 130, the second conductive surface 140, the first molecular wire 132, the second molecular wire 142, the capture agent 134, the reference compound 144, and the target entity 104 are described in more detail below.

Figure 2A:
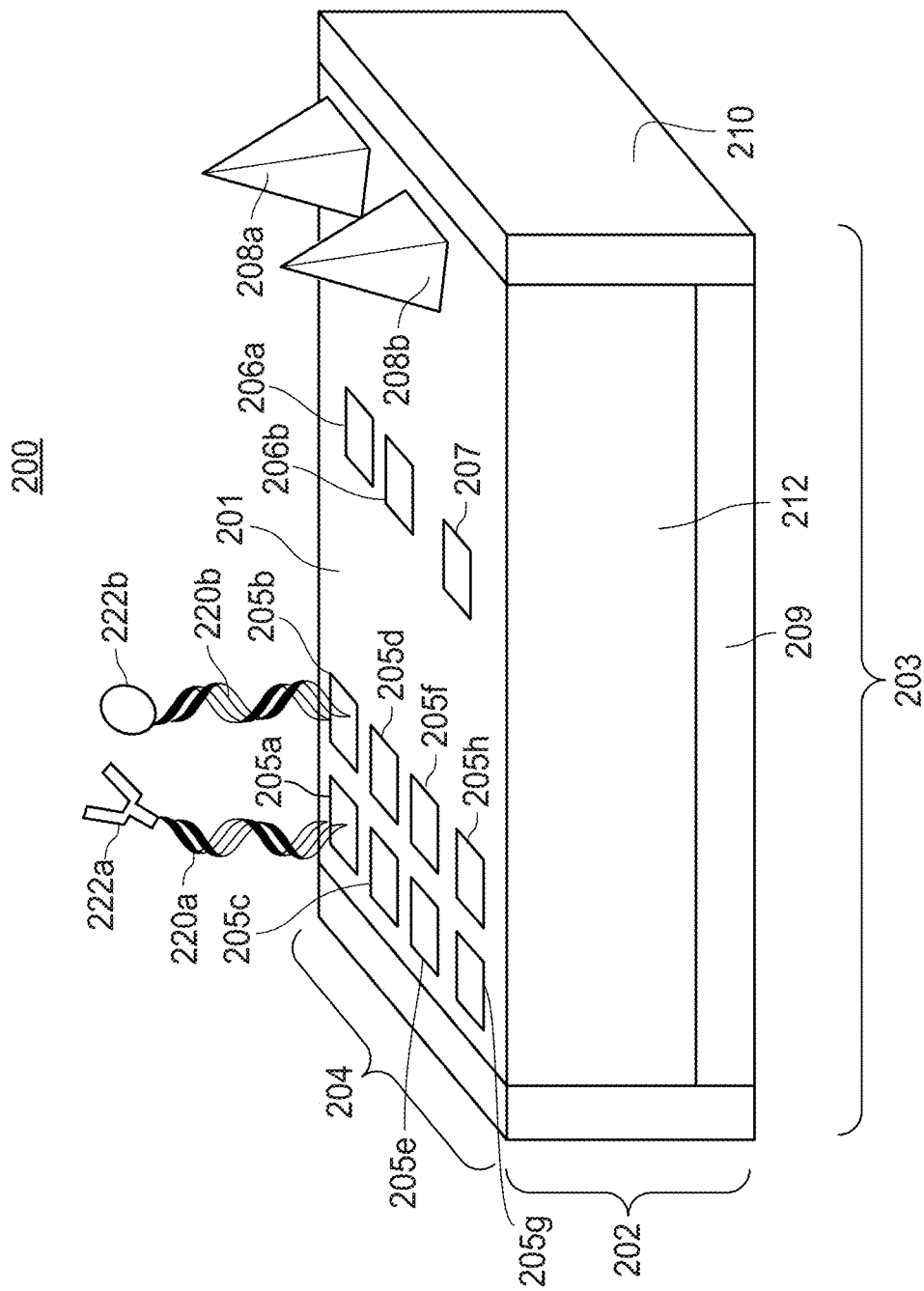
FIG. 2A is a perspective view of an example MNSDED implementation of the device of FIG. 1.

As noted above, the device 102 of FIG. 1 can be a MNSDED, in some embodiments. FIG. 2A is a perspective view of one such example MNSDED 200. The MNSDED 200 may be fabricated from a silicon wafer, for example. In the depicted embodiment, the MNSDED 200 has a primary surface 201 that is substantially flat, and which may be associated with the wafer surface in which the MNSDED 200 was fabricated. The MNSDED 200 may comprise a non-conductive housing with an outer surface corresponding to surface 201. In some embodiments, the surface 201 substantially comprises any suitable non-conductive dielectric material, such as silicon-oxide. The MNSDED 200 has a thickness (z-height) 202, and may be characterized by a major axis length 203 and a minor axis length 204. The length 203 may be between 50 and 100 micrometers, for example.

The surface 201 contains a plurality of pads (EEBIPs) 205a-h, which are electrically conductive surfaces. In some embodiments, the surface 201 also includes a plurality of communication bus pads 206a-b, which are electrically conductive areas that allow the MNSDED 200 to communicate electrically to a test process, and/or includes a solution-to-bulk silicon connection pad 207, which serves as a potential "ground" reference for electrical measurements with respect to cell surfaces or other surfaces or objects in the environment (e.g., biological or chemical solution) with the MNSDED 200. The solution-to-bulk silicon connection pad 207 may be coated with a conductive polymer or a polyelectrolyte layer to modify its electrical properties in solution, and may be electrically connected to the bulk silicon of the MNSDED 200. In other embodiments, the MNSDED 200 may include different numbers of pads 205, 206, and/or 207, and/or pads 206 and/or 207 may be omitted.

FIG. 2A depicts an embodiment in which the effector mechanism(s) 118 include a pair of nano-needles 208a-b (e.g., serving as an anode and cathode, respectively), each of which projects up substantially from the surface 201. The bottom 209 of the MNSDED 200 is comprised of a material which is not susceptible to the action of an etch liftoff chemistry. The bottom 209 may be comprised of a silicon-oxide or other insulating layer upon which the MNSDED 200 is fabricated. The sides 210 of the MNSDED 200 may be made of a different material (e.g., silicon nitride) that is also resistant to the liftoff chemistry and provide a substantially hermetic seal for those portions of the MNSDED 200.

Apart from select areas (e.g., the pads 205 associated with the binding site(s) 110 and the nano-needles 208), the surface 201 may be covered with protective molecules to ensure compatibility, stability, and/or other MNSDED 200 characteristics in the intended environment 100. If intended for use in a physiological solution, for example, the protective molecules may be biomolecules, lipids, constituents that typically make up vesicles, microsomes, or biologic membranes (e.g., red blood cell mimetic vesicles), polymers (e.g., PEG or PEI), or other suitable biocompatible molecules that ensure biocompatibility, non-immunogenic properties, and stability.

The MNSDED 200 also includes integrated circuitry layers 212, which may be built on a Silicon-on-Insulator ("SOI") wafer through microelectronic manufacturing processes. The integrated circuitry layers 212 may include the differential amplifier circuitry 112, logic circuitry 116, signaling circuitry 120, and energy harvesting circuitry 124 of FIG. 1 (and possibly driving circuitry of effector mechanism(s) 118 and/or the antenna(s) 122), for example. Each of the pads 205a-h (and the pads 206a-b and 207, if present), as well as the nano-needles 208a-b (if present), is electrically coupled to the integrated circuitry.

The surface 201 (or more generally, a non-conductive housing of which surface 201 is an outer surface) may support the antenna(s) 122 of FIG. 1, for example. In some embodiments, a loading compartment (not shown in FIG. 2A) is contained within the layers 212, and contains a therapeutic or imaging agent (e.g., part of the effector mechanism(s) 118) to be released or not released based on signals output by the logic circuitry 116.

Figure 2B:
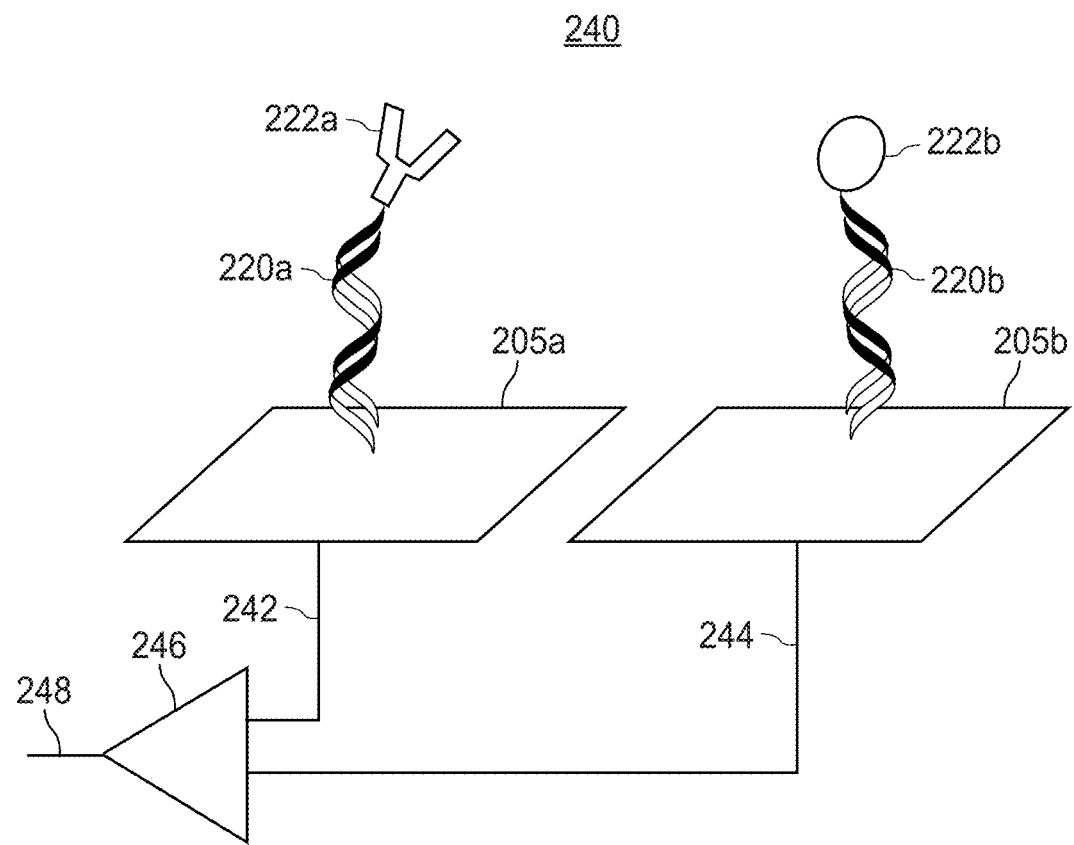
FIGS. 2B and 2C are enlarged views of a binding site of the example MNSDED shown in FIG. 2A, with example configurations of associated circuitry.

FIG. 2B is an enlarged view of a binding site 240 of the example MNSDED 200 shown in FIG. 2A. The binding site 240 may serve as the binding site 110 of FIG. 1, for example. The conductive target pad 205a is electrically coupled to a capture agent 222a, such as an antibody, through a first molecular wire 220a. The conductive reference pad 205b is electrically coupled to a reference compound 222b through a second molecular wire 220b. The first molecular wire 220a and the second molecular wire 220b are composed of chiral oligonucleotide multiplexes (e.g., duplexes) having identical nucleobase sequences and opposite chirality (i.e., absolute configuration). Accordingly, the first and second molecular wires are enantiomers having identical conductivity but orthogonal selectivity in hybridization. The capture agent 222a is exemplified as an antibody that can interact with (e.g., bind to) the target entity (e.g., an antigen). The reference compound 222b exhibits non-specific interactions with the environment. Components 242 and 244 represent the target input voltage and reference input voltage, respectively, component 246 represents a differential amplifier (e.g., differential amplifier circuitry 112 of FIG. 1), and component 248 represents the output voltage that the differential amplifier 246 provides to the logic circuitry (e.g., logic circuitry 116 of FIG. 1).

The first and second molecular wires 220a and 220b have identical lengths, are identically distant from their respective pads 205a and 205b, and have identical major axes or diameters. In some embodiments, each of molecular wires 220a and 220b has a length of at least about 0.3 nanometers, and no more than about 10 nanometers. In some embodiments, each of the molecular wires 220a and 200b is no more than about 2 nanometers distant from its respective pad 205a or 205b. In some embodiments, each pad 205a and 205b has a major axis or diameter that is no less than about 10 nanometers. In some embodiments, the pads 205a and 205b may be spaced about 50 nanometers apart.

Figure 2C:
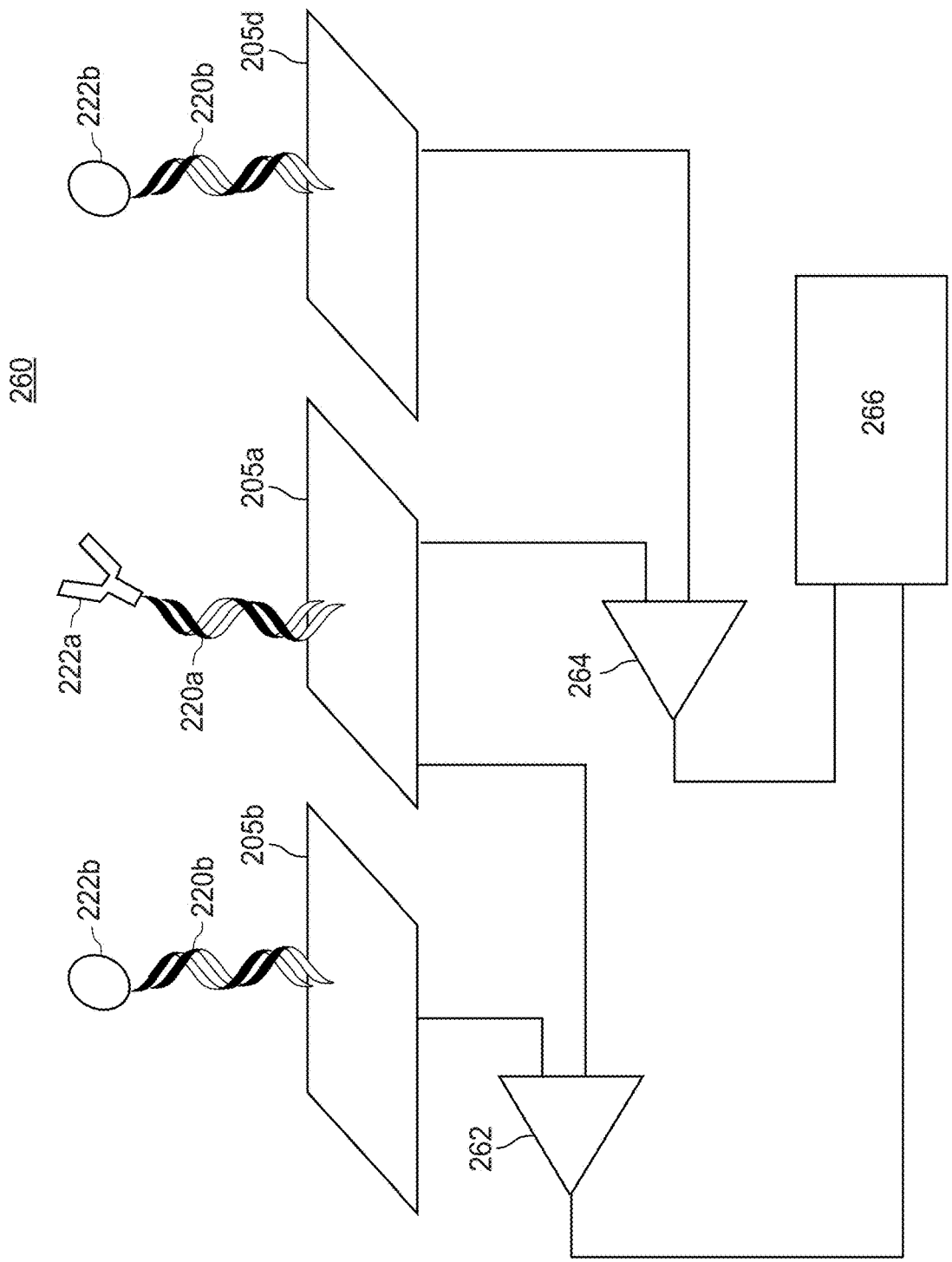

In other embodiments, the differential amplifier circuitry 112 of FIG. 1 is more complex than the configuration shown in FIG. 2B. As shown in connection with the example binding site 260 of FIG. 2C, for example, the differential amplifier circuitry 112 may include a first differential (e.g., sense) amplifier 262 with inputs electrically coupled to a target pad 205a and a first reference pad 205b, and a second differential (e.g., sense) amplifier 264 with inputs electrically coupled to the target pad 205a and a second reference pad 205d, with the outputs of the first and second differential amplifiers being inputs to a logic gate 266 of the logic circuitry 116. It is understood that other configurations of pads, amplifiers, and/or logic circuits are also possible.

Contrariwires—Harnessing Chirality for Selectivity

It is an objective of the present disclosure to design pairs of chiral oligonucleotide multiplexes, such as oligomeric nucleic acid duplexes, which function as molecular wires, possessing identical conductivity but orthogonal selectivity in multiplex (e.g., duplex) formation (i.e., in hybridization). As used herein, "multiplex" refers to the secondary structure of the oligonucleotides. The multiplexes can be, for example, duplexes (e.g., DNA-DNA, DNA-PNA, or PNA-PNA duplexes), triplexes (e.g., H-DNA), or quadruplexes (e.g., G-quadruplexes, i-motif DNA). In embodiments, one strand of the multiplex is coupled to the capture agent or reference compound, and the complementary strand of the multiplex is coupled to the appropriate conductive surface.

Figure 3:
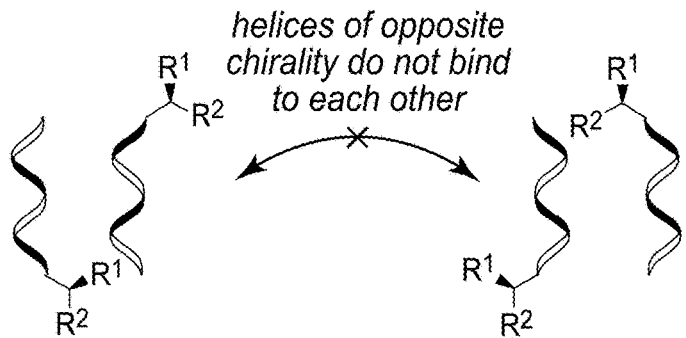
FIG. 3 shows chiral molecular wires having a stereospecific duplex-formation between strands of matching chirality (i.e., absolute configuration).
Figure 4:
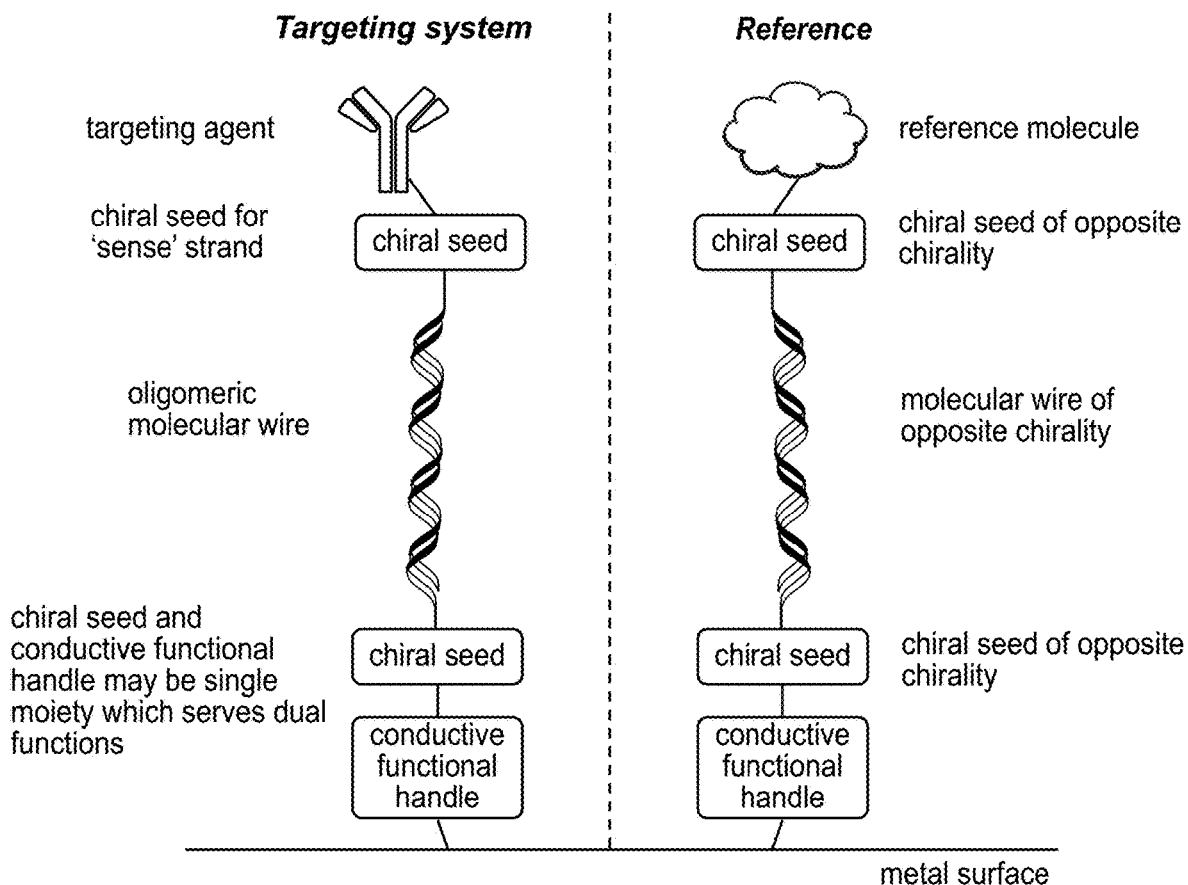
FIG. 4 is an exemplary schematic showing the composition of an antigen sensing system and a reference system.

These characteristics (identical conductivity but orthogonal selectivity in hybridization) can allow efficient installation of sensing (e.g., targeting) and reference agents on, for example, a MNSDED (required for common mode rejection), without necessitating the use of protecting groups. The present disclosure can accomplish this by leveraging the stereo specificity of nucleic acid pairing. The nucleobase sequence of both molecular wires are identical, but the multiplexes, such as the helices of duplexes, are of opposite absolute chiral configuration or "contrariwires." The backbone of DNA, for example, is comprised of alternating sugar and phosphate groups, while in PNA, this is replaced by a pseudopeptide structure. Both DNA and PNA exist as chiral helices, i.e., the two mirror image forms (referred to as left-handed and right-handed), are non-superimposable. A left-handed strand will only pair with a left-handed complement, and a right-handed strand will only pair with a right-handed complement (FIG. 3). One strand of the nucleic acid multiplex can be linked to a metal (e.g., gold) surface, for example, on a MNSDED EEBI pad, while a second strand of the nucleic acid multiplex (e.g., the complement of the first strand) can be linked to a capture agent (e.g. antibody) or reference protein. Enantiospecific multiplex formation, such as duplex formation, installs the capture agent and reference at the desired location on the metal (e.g., gold) surface. FIG. 4, for example, shows the composition of an exemplary antigen sensing system and reference system. PNA molecular wires of opposite chirality (i.e., absolute configuration) but identical nucleobase sequence allow for stereospecific duplex formation with identical conductivity. One strand of the PNA (the "sense" strand) can be conjugated to the capture agent component, while its complementary sequence can form the connection to the EEBIP (for example, gold) surface. Thus, the oligonucleotide multiplexes (e.g., duplexes) serve two distinct roles: first, as an "address label" for the sensing and reference agents, and second, as a molecular wire to form an electrical connection. In the "address label" role, the handedness of the helix ensures hybridization with the correct partner, while in the molecular wire role, both left-handed and right-handed helices have the same conductivity.

As described in greater detail herein, the structure of the molecular wires disclosed herein is comprised of five elements: an oligomeric backbone, nucleobases, an optional chemical moiety that attaches the capture agent or reference molecule (i.e., reference compound) to the oligonucleotide ("traceless" methods such as native chemical ligation may also be used to join the oligonucleotide and capture agent or reference molecule), an optional "chiral seed," and a chemical moiety (a functional handle) that attaches the oligonucleotide to the metal (e.g., gold) surface.

Backbone

The backbones of the chiral molecular wires disclosed herein (the first molecular wire and the second molecular wire) are identical and can comprise any chiral oligomer that places nucleobases in a 3-dimensional arrangement capable of conducting charge. It is not necessary that each monomer in the oligomer is chiral, but there should be enough chiral moieties to force the oligomer to favor one absolute configuration. As used herein, "absolute configuration" refers to the spatial arrangement of the atoms of a chiral molecular entity. Suitable oligonucleotides include deoxyribonucleic acid (DNA), ribonucleic acid (RNA), peptide nucleic acid (PNA), phosphorodiamidate morpholino oligomer (PMO), or any combination thereof. In some embodiments, the molecular wires comprise DNA. In various embodiments, the molecular wires comprise RNA. In some embodiments, the molecular wires comprise PNA. In some embodiments, the molecular wires comprise PMO. In embodiments wherein the molecular wires are duplexes, the molecular wires may comprise a DNA-DNA homoduplex, a RNA-RNA homoduplex, a PNA-PNA homoduplex, a PMO-PMO homoduplex, a DNA-RNA heteroduplex, a DNA-PNA heteroduplex, a DNA-PMO heteroduplex, a RNA-PNA heteroduplex, or a PNA-PMO heteroduplex. In some embodiments, each molecular wire comprises a DNA-DNA homoduplex, a PNA-PNA homoduplex, or a DNA-PNA heteroduplex. The oligonucleotides can be synthesized by any method known to those skilled in the art, such as by solid phase synthesis using, e.g., phosphoramidite building blocks.

Figure 8:
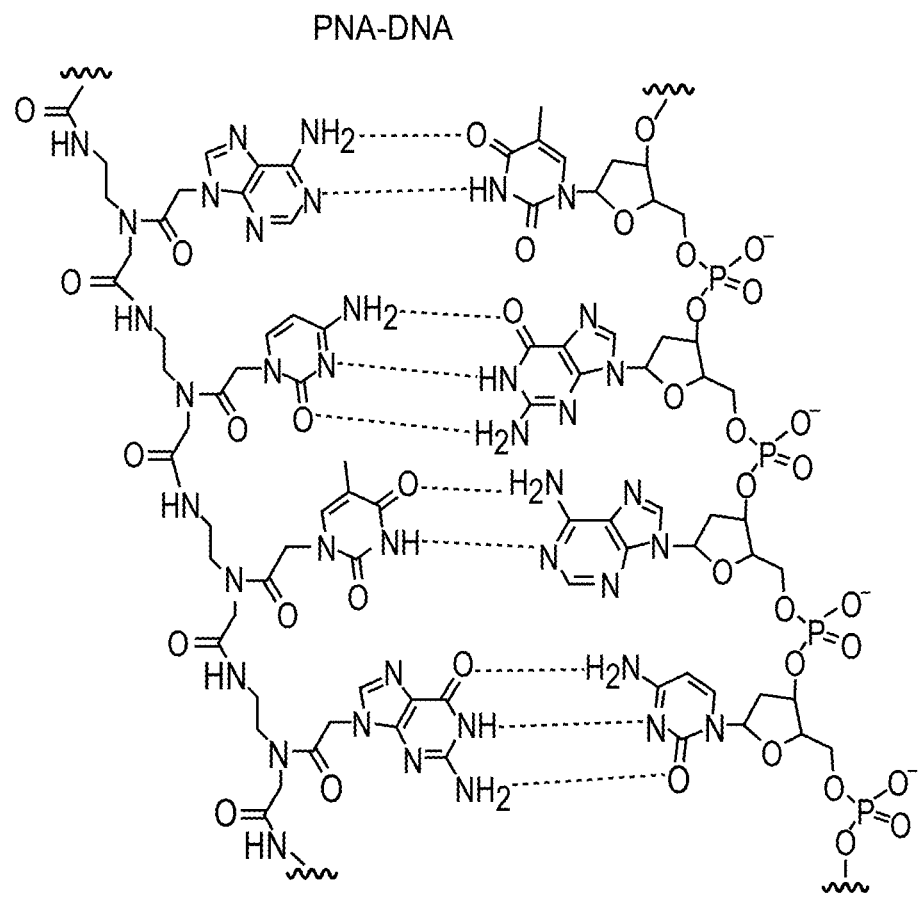
FIG. 8 shows an exemplary structure of a PNA-DNA heteroduplex.

Charge transfer in DNA occurs along the pi-array of nucleobases. Therefore, its conductivity can be improved by modulating both its physical structure and the energy levels of the relevant frontier molecular orbitals. Substituting the sugar-phosphate backbone with a more flexible pseudopeptide polymer (peptide nucleic acid or "PNA") allows the molecule to adopt more favorable conformations for charge transfer due to optimized pi-stacking between nucleobases. The PNA monomer can be based on the aminoethylglycine (aeg) motif (FIG. 5). Substitution at the γ position is also possible and confers unique chemical properties (vide infra). In contrast to the structure of B-DNA, PNA homoduplexes adopt a P-helix structure, characterized by a small twist angle and wide, deep major groove (FIG. 6). Flexibility is important for conductivity because the optimum conformation is dependent on the local nucleobase sequence. Thus, backbones that have been modified to increase rigidity tend to be poor molecular wires. A single strand of PNA can form a duplex with either PNA or DNA. These various backbone combinations provide a convenient chemical handle for modulating the physical properties of the molecular wire (FIGS. 7 and 8). The amino acid backbone of PNA offers the additional benefits of modular and scalable solid phase peptide synthesis. PNA wires are also advantageous because they can exhibit increased stability when administered to an in vivo system due to a large binding strength to complementary PNAs or DNAs (when compared to DNA-DNA homoduplexes), higher selectivity against base pair mismatches, and decreased degradation by proteases and nucleases. Employing noncanonical nucleobases is another strategy to optimize conductivity and/or annealing temperature. This can minimize the number of base pairs in complementary PNA/PNA or PNA/DNA sequences, thereby decreasing the overall length of the molecular wire while maintaining an annealing temperature greater than physiologic temperature and less than any temperature that would denature, degrade, or otherwise damage a targeting agent (i.e., a capture agent). This can ensure a minimal oligomeric wire size and improved conductivity, while maintaining oligomeric wire stability.

PMO are another class of oligonucleotides suitable for use in the molecular wires disclosed herein. These uncharged DNA analogs contain nucleobases attached to a backbone of methylenemorpholine rings linked through phosphorodiamidate groups. Like PNA, PMO are resistant to a variety of enzymes present in biologic fluids, which makes them particularly advantageous for use in in vivo applications.

In embodiments, the backbone of the oligonucleotide can be modified with one or more modifications commonly known to one skilled in the art. Contemplated backbone modifications can include, for example, incorporation of one or more phosphorothioate (PS) and/or phosphorodithioate linkages, which can be used to tune the properties of the molecular wire, such as to increase its stability.

Optional Chiral Seed

Figure 9A:
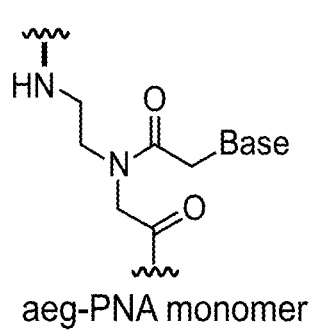
FIG. 9A shows an exemplary backbone motif of aminoethylglycine (aeg) PNA.
Figure 9B:
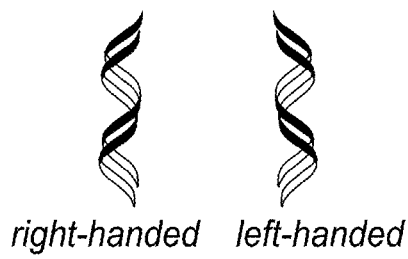
FIG. 9B shows an exemplary aeg-PNA backbone that is achiral, such that the helical structure does not adopt a preferred handedness.
Figure 9C:
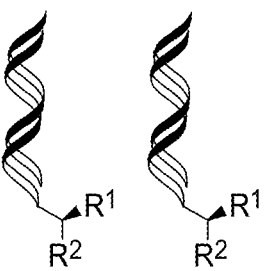
FIG. 9C shows an exemplary chiral unit within the duplex that will induce a preferred handedness.

In embodiments wherein the backbone comprises chiral monomers (e.g., DNA), the absolute configuration or "handedness" of the overall structure (e.g., of the DNA helix) is determined by the stereocenters in the backbone. In contrast, the aminoethylglycine backbone motif of aeg-PNA is achiral (FIG. 9A), and the overall structure does not favor one absolute configuration. In bulk solution, these PNA molecules exist as a 50:50 mixture of both left-handed and right-handed helices that can interconvert (FIG. 9B). However, a chiral moiety ("chiral seed") situated along the PNA strand can induce a preferred handedness in the structure (FIG. 9C). The chiral seed can be an amino acid (natural or unnatural), or a gamma-substituted PNA monomer. Suitable compounds capable of inducing chirality in PNA are well known to those skilled in the art (e.g., D- or L-lysine or D- or L-arginine). The chiral seed can be located at the 5'- or 3' termini of the PNA strand, in the middle of the sequence, or any combination thereof. In some embodiments, the PNA backbone includes one chiral moiety (i.e., chiral seed). In some embodiments, the PNA backbone includes, 2, 3, 4, 5, or more chiral moieties (i.e., chiral seeds). It is not necessary for every monomer to be chiral in order for the overall oligomer to strongly favor one enantiomer over the other. The achiral, aeg monomer confers higher conductivity, so the optimal ratio of achiral:gamma-substituted monomers will balance the requirements for both conductivity and configurational stability (in the relevant environment in which the device will be utilized, e.g. physiological conditions, as well as manufacturing conditions). The chiral seed(s) can be incorporated into the backbone of an otherwise achiral olionucleotide by any method known in the art for oligonucleotide synthesis, such as solid phase synthesis.

Nucleobases

The molecular wires disclosed herein (e.g., the first and second molecular wires 132, 142 of FIG. 1) are composed of identical nucleobase pair sequences, and thus, possess identical conductivity. Exemplary structures of nucleobases that can be incorporated into the molecular wires are shown in FIG. 10. These exemplary structures include, but are not limited to, any of the canonical nucleobases found in DNA and RNA, or any additional non-canonical nucleobases that can enable electrical conductivity properties. Non-canonical nucleobases enable increased permutations of base sequences beyond the canonical nucleobases. These non-canonical nucleobases enable tuning of the energy of the frontier molecular orbitals, thereby allowing increased overall molecular wire conductance. Any of these nucleobases can be used in the present disclosure, in any order. Size, hydrogen-bonding, and dispersion interactions enforce selective pairing of nucleobases. These pairing rules inform the overall design of the complementary strands. Additionally, the noncanonical nucleobases can be optimized to improve oxidative or pH stability, or resistance to enzymatic degradation. Examples of nucleobase modifications include incorporating a 5-methyl substituent on the nucleobase (e.g., 5-methylcytidine or 5-methyluridine), removing the base to form an abasic species, including a 2'-ribose substitution (e.g., 2'-OMe, 2'-CH$_2$CH$_2$OCH$_3$, or 2'-F), or introducing a bridged nucleic acid (e.g., locked nucleic acid (LNA), constrained ethyl bridged nucleic acid (cEt), ethylene-bridged nucleic acid (ENA)).

Conductive Functional Handle to Metal

Figure 11:
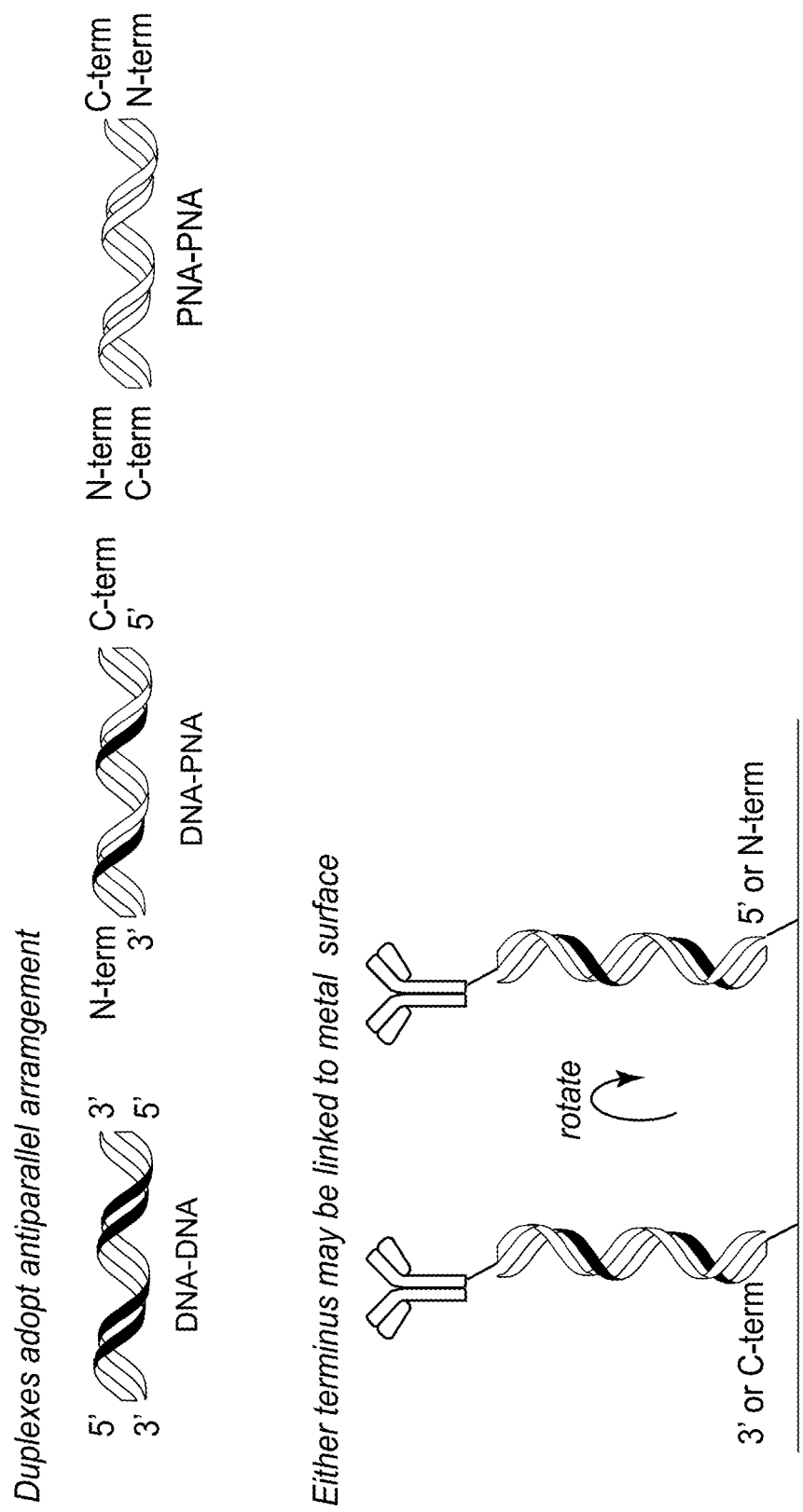
FIG. 11 shows exemplary molecular wires in an antiparallel arrangement that is favored in nucleic acid duplexes.

Like DNA, duplexes of PNA-DNA and PNA-PNA adopt an antiparallel arrangement. Either 5'- or 3'-terminus (in the case of DNA) or N- or C-terminus (in the case of PNA) may be linked to gold (or any other metallic surface that may participate in dative bonding), depending on the functional and synthetic requirements of the embodiment. For example, incorporating the 5'-terminus of DNA to the capture agent will force the N-terminus of a complementary PNA strand to be datively coupled to the metallic surface of the MNSDED EEBI pad (see FIG. 11 for a mutually exclusive and collectively exhaustive set of permutations).

The molecular wires described herein (e.g., the first and second molecular wires 132, 142 of FIG. 1) can be electrically coupled to their respective conductive pads or other surfaces (e.g., a metal such as gold) via a functional handle. The functional handle is a compound that is covalently bound to one strand of the multiplex, either at the backbone or on a nucleobase, and is capable of bonding to a metallic surface (e.g., gold). A variety of functional handles may facilitate linkage of the multiplex strand to the metallic surface. In some embodiments, the functional handle may include one or more of the following, alone or in combination: an amine, a thiol, heterocycles with nitrogen and/or sulfur and/or other heteroatoms, a carboxylate, a hydroxyl, an aldehyde, a ketone, a diazonium, an aryl azide, a halogenated aryl azide, a benzophenone, an anthraquinone, an alkyne, a biotin, a polypeptide or any other chemically active group. Those skilled in the art will understand that other functional handles could be employed in a similar manner to attach the multiplex strand to the metallic surface. In some embodiments, the functional handles can be less than about 2 nm in length to overcome Debye shielding for charge transfer from the multiplex strand, across the functional handle, and to the metallic surface.

In embodiments, the functional handle can be a nitrogen- or sulfur-containing compound in which the sulfur or nitrogen atom is bound to the metal (e.g., gold) on the conductive surface (or pad). In some embodiments, the functional handle is a nitrogen-containing compound. Suitable nitrogen-containing compounds include amino acids and derivatives thereof and alkyl amino compounds (e.g., a thymine 5-C2 amino linker). The alkyl amino functional handle (e.g., thymine 5-C2 amino compound) can be covalently tethered directly to a nucleobase rather than the backbone, which increases conductivity.

In embodiments, the functional handle is a sulfur-containing compound. Suitable sulfur-containing compounds include amino acids and derivatives thereof (e.g., cysteine, dithiols, and dithiocarbamates), thiaadamantanes (e.g., trithiaadamantane), and aryl thiols and derivatives thereof (e.g., thiophenol derivatives, benzyl mercaptan derivatives, thiophenanthrene derivatives).

Figure 13:
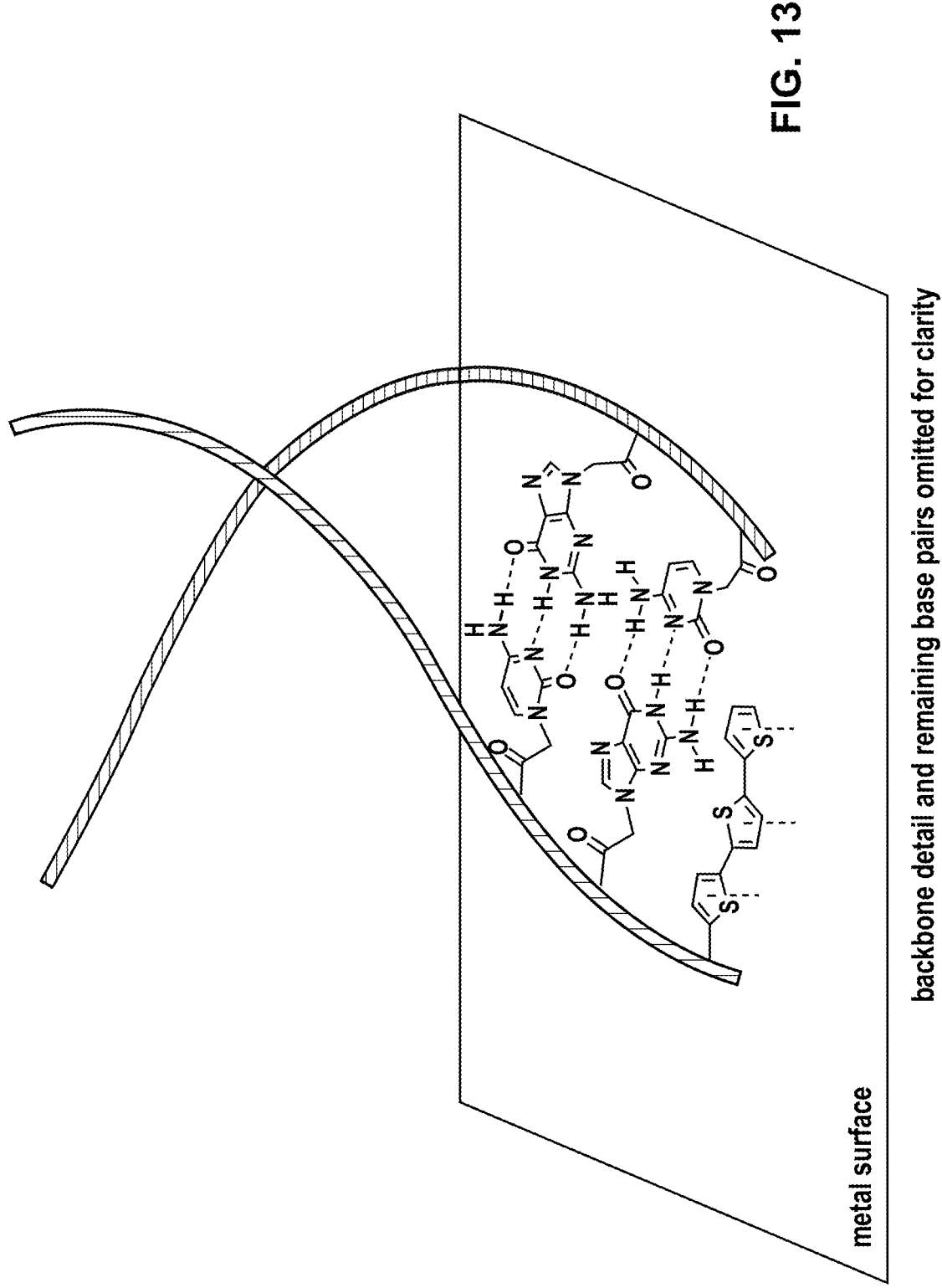
FIG. 13 shows exemplary thiophene-based molecules, which coordinate to gold (or other metallic EEBIP surfaces) via a conjugated pi-system and extend the pi-stacking of nucleobase molecular orbitals.

In some embodiments, the conductive functional handle comprises a sulfur-containing heterocycle that is capable of datively bonding to a metallic surface (e.g., gold). As used herein, "sulfur-containing heterocycle" refers to an aromatic ring system comprising at least one sulfur atom and 5- to 10-total atoms. The sulfur-containing heterocycle can include 1, 2, or 3 additional heteroatoms selected from N, O, or S. In some embodiments, the sulfur-containing heterocycle includes only 1 heteroatom, which is sulfur. The heterocycle may bond to the metal through just the heteroatom (i.e., $\eta^1$), or it may bond via an uninterrupted and contiguous series of atoms in the heterocycle. In the first case, the heterocycle coordinates to the metallic surface, such as an EEBIP surface, in an upright position through the lone pair on its heteroatom. In the second case, the plane of the heterocycle lies parallel to the metallic surface (i.e., $\eta^5$ in the case of thiophene), such as the EEBIP surface, allowing orbital overlap with both the metal surface and the nucleobases of the wire. This through-space conjugation minimizes series resistance of the overall structure. Such chemistry can advantageously bypass Debye shielding within physiologic environments. The most favorable hapticity can be determined by the specific thiophene or derivative thereof used. In some embodiments, the functional handle that datively bonds to the metallic surface comprises thiophene, benzothiophene, or a derivative of thiophene or benzothiophene. In some embodiments, oxidized thiophene oligomers may be incorporated into the conductive functional handle as this has been shown to improve conductance by decreasing the HOMO-LUMO gap. In some embodiments, the functional handle comprises thiahelicene, as further described below. FIG. 12 shows exemplary chemical moieties that can attach the molecular wire to a metal surface, such as the EEBIP surface. FIG. 13 shows a coordination mode where the pi-system is parallel to the surface, which may provide enhancements to conductivity as it allows continuous pi-stacking from the nucleobases to the metallic surface, such as an EEBIP surface. Additional chemical moieties may attach to a metal surface, such as to the EEBIP surface, as would be apparent to those skilled in the art.

The functional handles can be divided into two categories: chiral and achiral. In some embodiments, the functional handles on the first and second molecular wires (e.g., molecular wires 132 and 142) are identical and achiral. In some embodiments, the functional handles on the first and second molecular wires are enantiomers. Chiral functional handles can serve the additional role of a chiral seed to stabilize one absolute stereochemical configuration of the molecular wire, as detailed above, such as when the molecular wire includes an achiral PNA backbone. When the functional handles are chiral and enantiomers, one enantiomer forms the connection to the capture agent (e.g., antigen-capture agent) circuitry, while the opposite enantiomer forms the connection to the reference circuitry. Helical polythiophenes and helical fused thiophenes (FIG. 12) are a subclass of the thiophenes described above. Their unique chemical properties serve several purposes in this context. They are capable of dative bonding to the metal (e.g., gold) surface. They are known to be highly conductive, thus lowering the series resistance of the entire structure. Their inherently chiral nature also serves to seed achiral PNAs into the desired left-handed or right-handed absolute configuration. Enantiomerically pure helicenes can be synthesized enantioselectively or enantiospecifically by the addition of chiral substituents on the thiophene rings or by separating a racemic mixture of helicenes.

In the case of the achiral functional handles (for bonding to the metallic surface), additional conjugation to a chiral moiety (amino acids, amino acid derivatives, or gamma-modified PNA monomer as described in the Chiral Seed section, above) may be utilized to provide stereocenter(s) necessary for chiral induction and to ensure configurational stability.

Molecular Wire Attachment to a Capture Agent or Reference Molecule (i.e., Reference Compound)

The first and second molecular wire electrically couple a conductive surface to a capture agent (i.e., target or targeting compound) and a reference compound (i.e., reference molecule), respectively.

The capture agent can be any chemical or biological compound capable of binding to a target entity, such as a chemical or biological entity. As used herein, the term "bind," the term "binding," or the term "bound" refers to any type of chemical or physical binding, which includes but is not limited to covalent bonding, hydrogen bonding, electrostatic interactions, hydrophobic interactions, London dispersion forces, biological tethers, transmembrane attachment, and cell surface attachment. As used herein, the term "interaction" refers to attractive forces between molecules and between non-bonded atoms. As used herein, the term "binding event" refers to the act of a chemical or biological compound binding to a target entity.

As used herein, "target," "target entity" or "chemical or biological entity" refers to a chemical (a compound that is not derived from a biological source) or biological compound that can specifically interact with (e.g., bind to) the capture agent. The target entity can include any biological system of interest, such as organs, tissues, cells or any portion thereof and may include in vitro or in vivo biological systems or any portion thereof. Examples of the target entity include antigens, viruses, and receptors on diseases associated cells (DACs).

The reference compound is a chemical or biological compound that is electrically similar to the capture agent (e.g., similar impedance to the capture agent) but does not specifically bind to a biological or chemical entity found in its environment. Thus, the reference compound has non-specific interactions with its environment.

Suitable capture agents and reference compounds include small molecules, peptides, proteins, carbohydrates, lipids, and oligonucleotides. As used herein a "small molecule" is an organic compound having a molecular weight of less than about 900 daltons that can bind to a biological compound or regulate a biological process. Contemplated small molecules include, e.g., vitamins (e.g., folic acid, biotin), neurotransmitters (e.g., acetylcholine, dopamine, gamma-aminobutyric acid), and drugs (e.g., a chemotherapeutic agent). Contemplated peptides include, e.g., those than can bind to a specific target molecule (e.g., aptamers). Contemplated proteins include, e.g., glycoproteins (e.g., transferrin), antibodies (e.g., monoclonal antibodies), and enzymes. Contemplated carbohydrates include, e.g., monosaccharides (e.g., glucose, fructose, ribose, galactose) and polysaccharides (e.g., sucrose, lactose). Contemplated lipids include, e.g., triacylglycerols, terpenoids, steroids, prostaglandins, and phospholipids. Contemplated oligonucleotides include, e.g., DNA, cDNA and RNA. In particular, capture agents may be antibodies against certain surface cell receptors or markers.

In some embodiments, the capture agent and/or reference compound is an antibody. The term "antibody" or "immunoglobulin" refers to a polypeptide or protein substantially encoded by an immunoglobulin gene or immunoglobulin genes, or fragments thereof, which is reactive with an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab, Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. The "Fc" portion of an antibody refers to that portion of an immunoglobulin heavy chain that comprises one or more heavy chain constant region domains, CH1, CH2 and CH3, but does not include the heavy chain variable region. Therefore, the term "antibody" also includes antigen binding forms of antibodies (e.g., Fab', F(ab')2, Fab, Fv, rIgG and others) that are known to those skilled in the art, as well as genetically engineered forms such as chimeric antibodies (e.g., humanized murine antibodies), heteroconjugate antibodies (e.g., bispecific antibodies), recombinant single chain variable fragments ("scFv"), disulfide stabilized Fv ("dsFv") fragments, or pFv fragments.

In embodiments, the capture agent may include a binding region that is specific to a particular chemical functional group, chemical bond, or combination of chemical functional groups, steric regions, or other chemically related entities where interactions may occur. The capture agent may also include a binding region specific for a receptor expressed on a cancer cell, an autoimmune-associated cell, an infectious disease associated cell, or any other DAC. These receptors may be specific to membrane-associated receptors, receptors that are internalized, receptors that transcytose, receptors that are associated to lysosomal trafficking, or receptors that are associated with trafficking to any other subcellular compartment. In various embodiments, the reference compound may include, but is not limited to, small molecules, polymers (e.g. PEG, PEI etc.), peptides, glycoproteins, proteins (e.g. antibodies, antibody fragments, albumin), nucleic acids, lipids (e.g. palmitate), small molecules, and any other molecule or biomolecule that does not specifically bind to the target entity.

A variety of techniques may be used to link a capture agent (or targeting agent) or reference molecule (i.e., a reference compound) to a molecular wire, such as a PNA or DNA molecular wire. In the case of a peptide or PNA aptamer, the entire structure (peptide+PNA molecular wire) may be synthesized by solid phase peptide synthesis or other method as would be recognized by those skilled in the art of peptide synthesis. In the case of an antibody, antibody fragment, or protein, a "traceless" method such as expressed protein ligation or native chemical ligation may be used. In this case, the Cys residue resulting from the ligation procedure may further serve as the chiral seed for the PNA strand. Alternatively, a variety of functional handles may be used for conjugation (FIG. 14). The antibody/antibody fragment/protein may be engineered to introduce unnatural reaction handles (or moieties that facilitate reactive chemistry), or to reduce the number of reactive amino acid side chains (for example by genetically modifying Cys residues to Ser, leaving only one Cys residue than can react with a functional handle).

In some embodiments, conjugating the targeting agent or reference compound to the molecular wire can be carried out by reacting an electrophilic reactive group of one partner of the conjugation with a nucleophilic reactive group of the other partner of the conjugation. Examples of electrophilic reactive groups include carboxyl, N-hydroxysuccinimide (NHS), tosylate (Tos), mesylate, triflate, carbodiimide, hexafluorophosphate, acyl chloride, anhydride, ester, succinimide ester, alkyl halide, sulfonate ester, maleimido, haloacetyl, and isocyanate. Examples of nucleophilic reactive groups include amino, thiol, or hydroxyl groups. In some embodiments, conjugation of the targeting agent or reference compound to the molecular wire can be carried out using click chemistry. Azide-alkyne cycloaddition, or "click reaction," is wide in scope and easy to perform, uses only readily available reagents, and is insensitive to oxygen and water. In some embodiments, the click reaction is a cycloaddition reaction between an alkynyl group and an azido group to form a triazolyl group. In some embodiments, the click reaction uses a copper or ruthenium catalyst. In some embodiments, the reaction is strain-promoted, (by destabilizing the alkyne partner, as in difluorinated cyclooctyne or dibenzocyclooctyne) and thus does not require a metal catalyst. Suitable methods of performing click reactions are described in the art. See, for example, Kolb et al., *Drug Discovery Today* 8:1128 (2003); Kolb et al., *Angew. Chem. Int. Ed.* 40:2004 (2001); Rostovtsev et al., *Angew. Chem. Int. Ed.* 41:2596 (2002); Tornoe et al., *J. Org. Chem.* 67:3057 (2002); Manetsch et al., *J. Am. Chem. Soc.* 126:12809 (2004); Lewis et al., *Angew. Chem. Int. Ed.* 41:1053 (2002); Speers, *J. Am. Chem. Soc.* 125:4686 (2003); Chan et al. *Org. Lett.* 6:2853 (2004); Zhang et al., *J. Am. Chem. Soc.* 127: 15998 (2005); and Waser et al., *J. Am. Chem. Soc.* 127:8294 (2005). Additional methods and techniques for conjugating the capture agent or reference compound to the molecular wire can be found in, e.g. Hermanson, G. Bioconjugate Techniques, $3^{rd}$ Ed, Academic Press, 2013.

Molecular Wire Length

The length of the molecular wire is determined by balancing a number of competing factors. Longer sequences have higher melting points ($T_m$, the temperature at which 50% of the nucleic acid has denatured from double-stranded to single-stranded). In some embodiments, the ideal $T_m$ is lower than the denaturation temperature of the capture agent (e.g., antibody) but higher than human body temperature. Other factors that affect $T_m$ include nucleobase sequence (e.g., $T_m$ increases with higher GC content relative to AT content) and backbone structure (the $T_m$ of PNA-PNA homoduplexes is greater than the $T_m$ of PNA-DNA heteroduplexes, which is greater than the $T_m$ of DNA-DNA homoduplexes).

Figure 15:
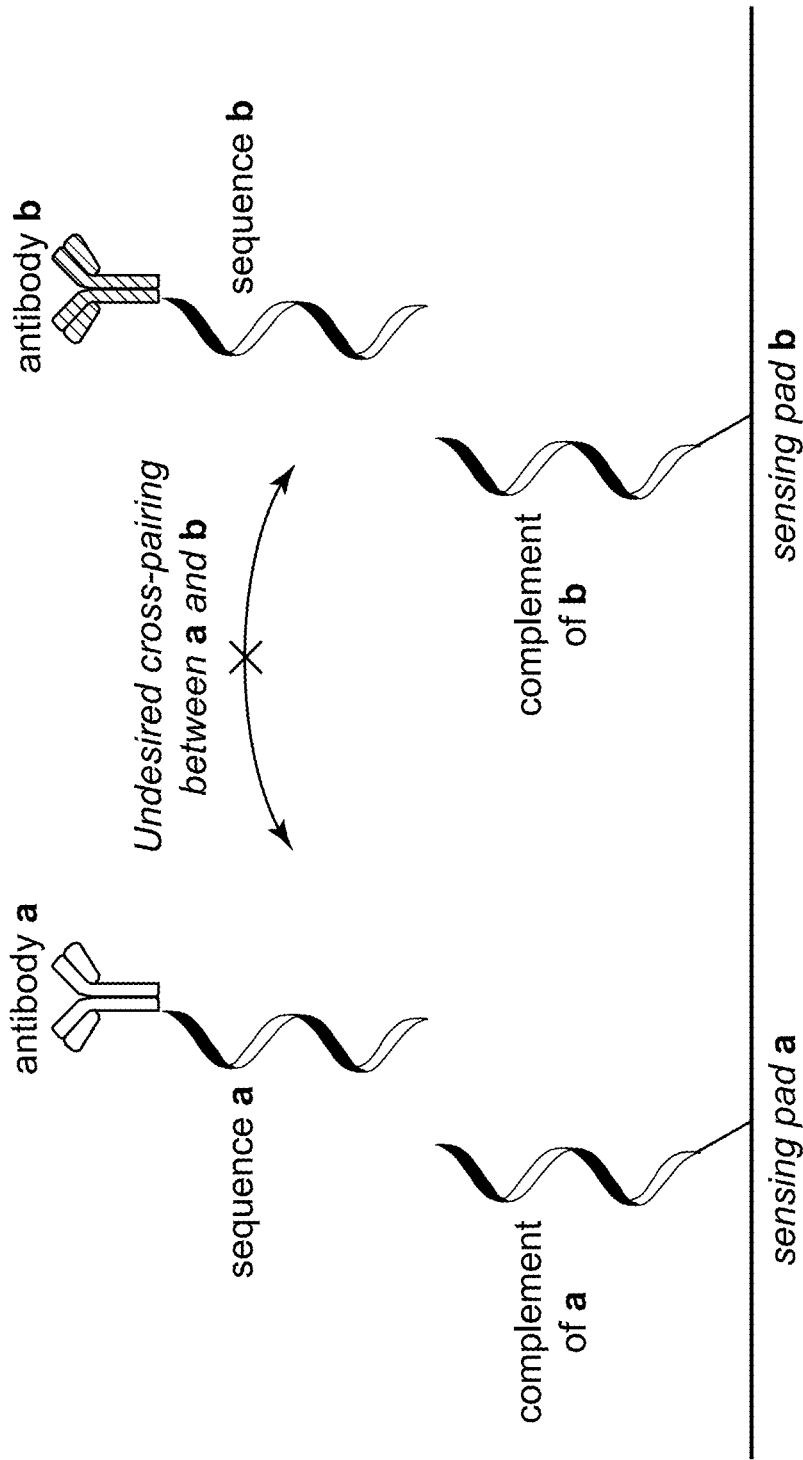
FIG. 15 shows a schematic highlighting that nucleic acid sequences can be selected to eliminate the potential for cross-pairing (antibodies a and b are not a capture agent/reference pair, thus they are conjugated to oligonucleotides with different base pair sequences).

The nucleobase sequence needs to be long enough to allow unique nucleobase combinations for each different capture agent and reference molecule (i.e., reference compound) pair that provides input to associated logic circuits (such as that in a MNSDED). Furthermore, it is not sufficient for the nucleobases sequences to be strictly unique, but they must be different enough to prevent undesired cross-pairing between different capture agents/reference molecules (ie undesired cross-pairing between capture agent a and capture agent b, or between reference a and reference b. See FIG. 15).

Note that the effect of base pair mismatches is dependent on the molecular wire backbone composition, where base-pair mismatches are more destabilizing in a PNA-DNA duplex compared to DNA-DNA. On average, a single base pair mismatch in a PNA-DNA duplex leads to 15° C. decrease in $T_m$ compared with 11° C. for DNA-DNA.

The molecular wires need to be designed to meet the above criteria with a minimum number of nucleobases (i.e., as short as possible), as longer oligomers impair conductivity (and are also more difficult to synthesize).

Lithographic Techniques for Bio-Compatible Lithography of Molecular Wires

The methods provided herein include biocompatible lithographic techniques. One such technique is the utilization of a chiral oligonucleotide strand (e.g., ssDNA) that is attached to the metallic (e.g., gold) surface, which may then bind to a complementary chiral oligonucleotide strand (e.g., complementary ssDNA) that itself is bound to a capture agent. Photolithography can be used to bind the chiral oligonucleotide strand (e.g., ssDNA) to the correct conductive pad. A predesigned group of pads (EEBIPs) may be left exposed during lithographic patterning through mask-based patterning, while covering with triple layer (described herein) all other conductive pads that are to remain unreacted with the specific chiral oligonucleotide strand (e.g., ssDNA sequence). This lithographic patterning may employ a triple layer using materials that are well known to those skilled in the art of photolithography. For example, the triple layer may consist of or comprise a biological protection layer (e.g., SU-8 or PEG), an anti-reflective coating (ARC), and a photoresist (PR) layer (ideally but not limited to known biocompatible resists such as SU-8) that may contain a top coat (e.g. if an immersion photolithography process is indicated). The lithographic patterning may be accomplished through a standard spin-expose-develop (SED) process that is itself well known to those skilled in the art of photolithography.

Subsequently exposed conductive pads may be treated with an enantiomerically pure chiral oligonucleotide strand (e.g., an enantiomerically pure ssDNA oligomer) that contains a moiety capable of bonding to the metal surface (e.g., a sulfur heterocycle, such as thiophene). Once the chiral oligonucleotide strand (e.g., ssDNA oligomer) is bonded to the metal surface (e.g., datively and/or covalently linked to the pad), the triple layers may be removed through conventional processing (e.g., processes that utilize biocompatible solvents that do not damage oligonucleotides (e.g., ssDNA), or other known solvents such as N-methyl-2-pyrrolidone (NMP), followed by solvent removal by heating to 80° C.). The biocompatible protectant layer deposition, ARC deposition, PR deposition, SED, ssDNA conjugation, and PR/ARC removal process can then be reproduced at a different location on the metal surface with oligonucleotide strands (e.g., ssDNA oligomers) of identical nucleobase sequence but opposite absolute stereochemical configuration (opposite enantiomer, or "handedness"), producing a pair of pads which will eventually correspond to a capture agent and reference agent. The whole process can be repeated to produce multiple pairs of pads.

After all the desired pairs of conductive pads have been conjugated to the chiral oligonucleotide strand (e.g., ssDNA), capture agents (antibodies, etc., as described above) can be conjugated to complementary oligonucleotides (e.g., sequences of DNA) with the appropriate chirality (i.e., the chirality, or handedness, that matches the chirality of the oligonucleotide, such as ssDNA, attached to the conductive surface at the desired location). The subsequent coupling of the capture agents to their intended location on the conductive surface will occur through hybridization of oligonucleotide strands (e.g., DNA sequences) with complementary nucleobase sequences and matching absolute stereochemical configuration (i.e., such that both partners are the same enantiomer), where annealing of the complementary sequences of oligonucleotides (e.g., ssDNA) can be thermally controlled such that the annealing takes place at no less than 5° C. below the melting temperature ($T_m$) of the complementary strands of oligonucleotides (e.g., ssDNA). For example, in some embodiments, cDNA sequences may be designed such that the $T_m$ is 55° C., and the reaction mixture may be incubated between about 50° C. and about 55° C., where 50° C. is no more than 5° C.

below the T$_m$, and with the additional constraint that the temperature of the reaction does not exceed the temperature at which the capture agents and reference compounds begin to degrade or denature. This hybridization reaction may be conducted in an aqueous environment, with a gently buffered solution (e.g., less than 50 mM sodium phosphate, pH 7.4). Once all complementary oligonucleotides (e.g., DNA) have been annealed, the remaining surface of the metal may be back-filled (e.g., with a methoxyl-(n-alkyl)-thiol monolayer) that will further protect each pad from non-specific binding of environmental components (e.g., plasma proteins, interstitial proteins, etc.). Protection of the metal with a monolayer such as methoxy-(n-alkyl)-thiol may also happen before chiral oligonucleotide (e.g., ssDNA) conjugation (with ssDNA subsequently displacing some alkyl thiol molecules) as a way to control the density and uniformity of the chiral oligonucleotide (e.g., ssDNA). Through this process, the target pad (or more generally, first conductive surface) will associate with a chiral oligonucleotide strand (e.g., a ssDNA sequence), which will anneal with a complementary oligonucleotide strand (e.g., a complementary ssDNA) having a matching absolute stereochemical configuration, which in turn is bound to the capture agent, thus forming the first molecular wire. Likewise, the reference pad (or more generally, second conductive surface) will associate with a chiral oligonucleotide strand (a ssDNA sequence) having opposite handedness than the oligonucleotides of the first molecular wire, which will anneal with a complementary oligonucleotide strand (e.g., a complementary ssDNA) having matching absolute stereochemical configuration, which in turn is bound to the reference compound, thus forming the second molecular wire. Accordingly, the first and the second molecular wires have opposite stereochemical configurations and are enantiomers. The process described herein is advantageous because the chirality of the olignonucleotides imparts selectivity, acting as an "address label" for the capture agent and the reference compound during assembly of the system, minimizing the number of steps required during fabrication.

Figure 16A:
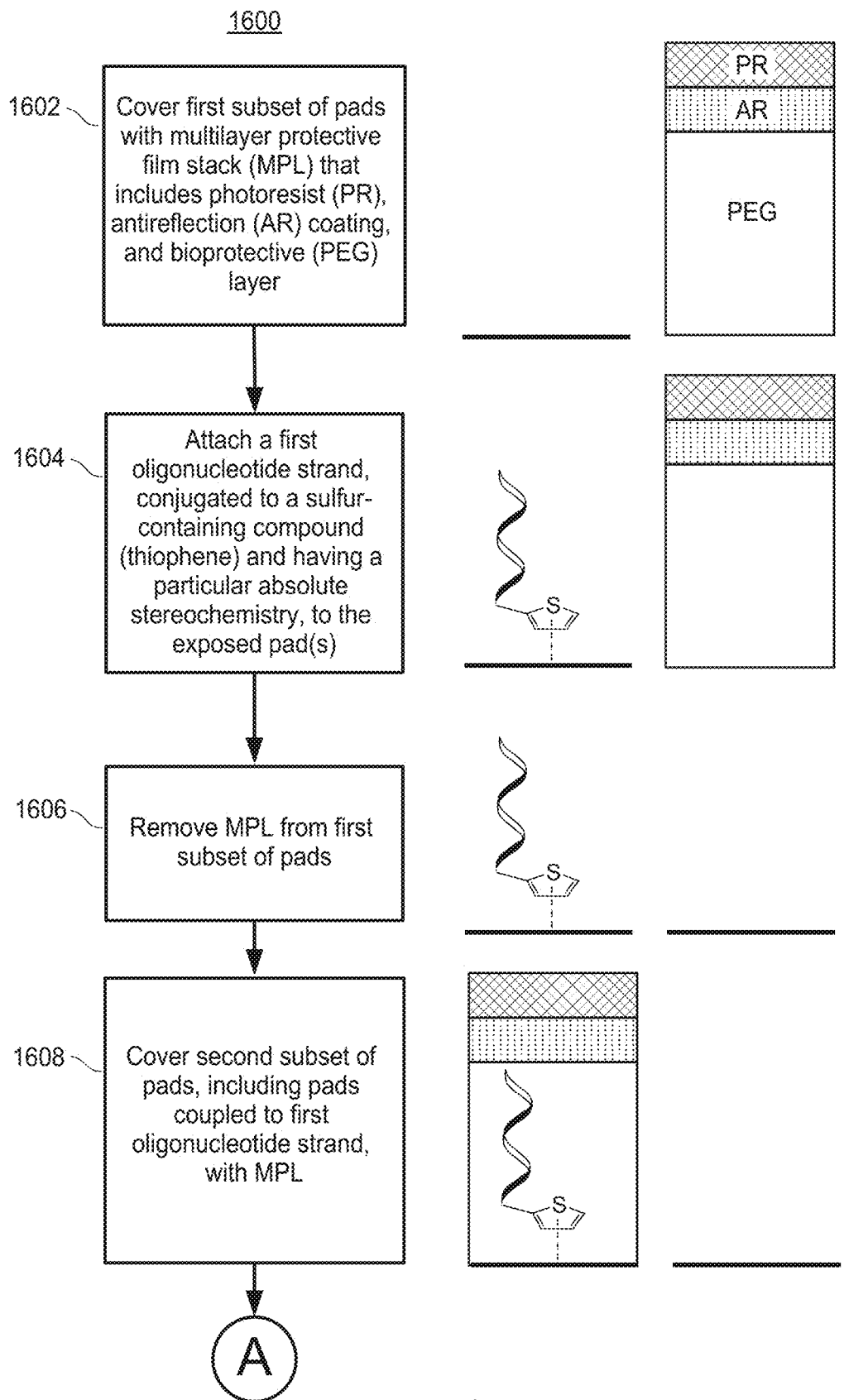
FIGS. 16A and 16B are portions of a flow diagram of an example biocompatible lithography process for fabricating one or more MNSDEDs.
Figure 16B:
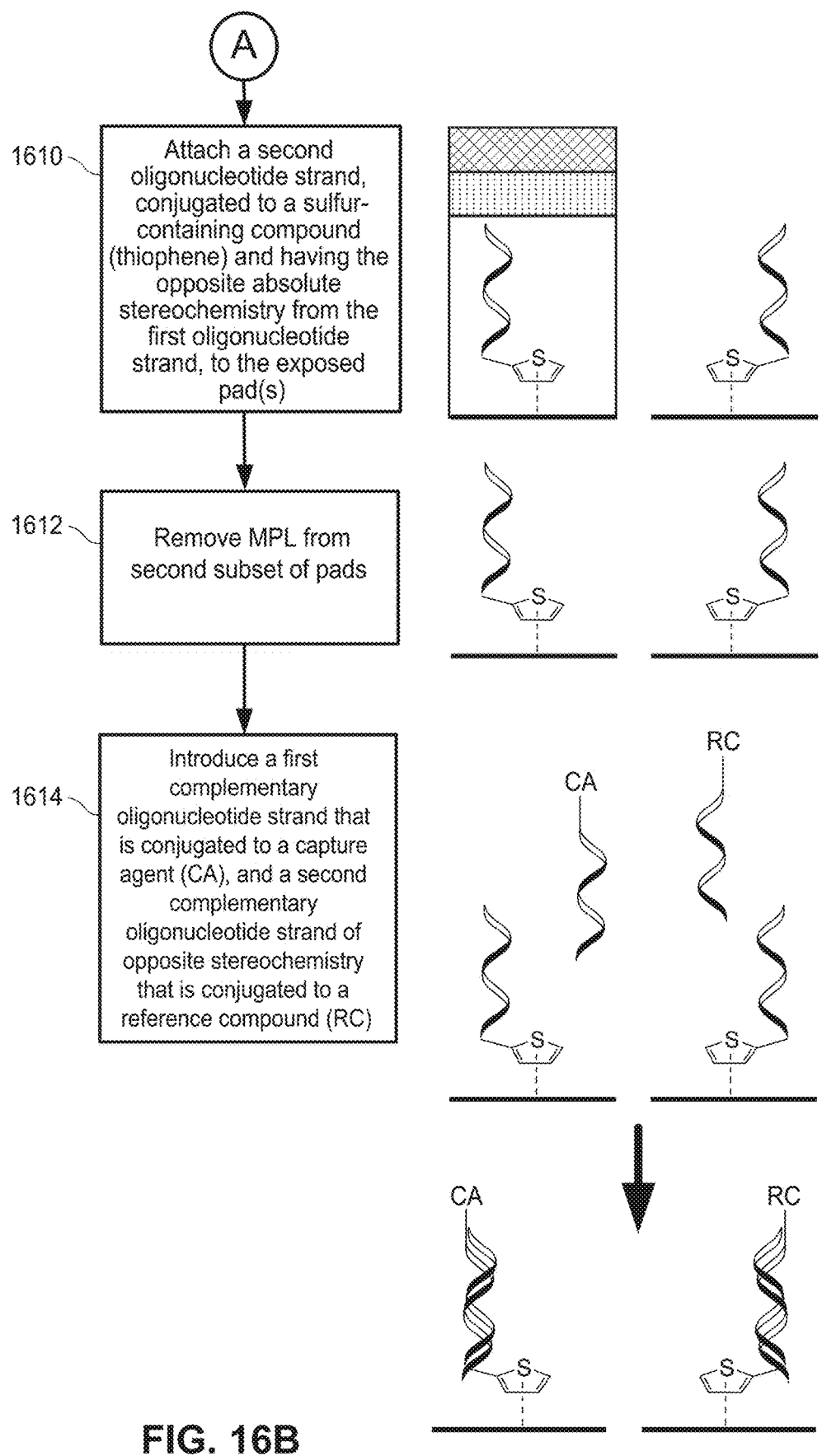

FIGS. 16A and 16B are portions of a flow diagram of an example biocompatible lithography process 1600 for fabricating one or more MNSDEDs (e.g., the MNSDED 200 of FIG. 2A). Exemplary chemical structures and reactions, corresponding to the steps of the bio-compatible lithography process 1600, are also depicted in FIGS. 16A and 16B. Variations to and deviations from this exemplary process 1600 for fabricating MNSDEDs, depending on specific MNSDED end-uses and applications, should be readily apparent to one of ordinary skill in the relevant art.

In step 1602, a multilayer protective film stack (MPL), comprising or consisting of a photoresist (PR), antireflection (AR) coating, and bioprotective (e.g., PEG) layer, covers a first subset of the pads (i.e., a first set of one or more of the pads) fabricated on the MNSDED, leaving the remaining pad(s) exposed. In step 1604, a first oligonucleotide strand(s) conjugated to a thiol-containing compound (as the functional handle) and having a particular absolute stereochemistry is attached to the exposed pad(s). In step 1606, the MPL is removed from the first subset of pads that were previously covered in step 1602, utilizing techniques well-known in the art. In step 1608, a second subset of pads (including those pad(s) already coupled to the first oligonucleotide strand) are covered in MPL through standard lithographic techniques, leaving uncovered only pads that are intended to be coupled with a second oligonucleotide strand. In step 1610, a second oligonucleotide strand that is conjugated to the same thiol-containing compound (as the functional handle) and has the same sequence as the first oligonucleotide strand, but having opposite absolute stereochemistry relative to the first oligonucleotide strand, is attached to the exposed pad(s). In the case where the thiol-containing functional handle is achiral, the functional handle will be identical for both pads. In step 1612, the MPL is removed from the second subset of pads that were previously covered in step 1608, utilizing techniques well-known in the art.

In step 1614, complementary first and second oligonucleotide strands having opposite stereochemical configurations from each other are introduced to the system. The complementary first oligonucleotide strand is conjugated to a capture agent and the complementary second oligonucleotide strand is conjugated to the reference compound. These complementary oligonucleotide strands hybridize with the oligonucleotide strands coupled to the pads having the same absolute stereochemistry, thereby forming the multiplexes (e.g., duplexes) of the first and second molecular wires. Advantageously, due to the specificity of the first and second oligonucleotide strands, there is no need to sequentially cover and uncover the target- and reference-side pads/strands when introducing the first and second complementary oligonucleotide strands, thereby reducing fabrication time and cost. Thus, the first and second complementary oligonucleotide strands can be introduced in a single step, e.g., within a single solution that includes both strands. Additionally, in this process, the capture agent and reference compound are not introduced until after all photolithographic patterning steps are complete, thus protecting them from harsh photolithography conditions (the capture agent and reference compounds may be more delicate than the oligonucleotide molecular wires). While not shown in FIGS. 16A and 16B, the biocompatible lithography process 1600 may include additional steps. For example, in a first additional step after step 1614, and after all pads are coupled to their respective oligonucleotide strands, all (or substantially all) surfaces may be covered in protective layer(s) comprised of biocompatible protective molecules, and in a subsequent, second additional step, liftoff trench patterning resist may be applied in preparation for separating the MNSDED(s) from the silicon wafer using an etch lift-off process.

Accordingly, disclosed is a method of fabricating a device as described herein. The method comprises fabricating a plurality of conductive surfaces (e.g., pads) on a primary surface (e.g., silicon wafer and/or housing), wherein the plurality of conductive surfaces include one or more capture surfaces and one or more reference surfaces; attaching a first molecular wire to each capture surface of the plurality of conductive surfaces; attaching a second molecular wire to each reference surface of the plurality of conductive surfaces; conjugating to each of the first molecular wires a capture agent that can interact with a target entity; and conjugating to each of the second molecular wires a reference compound that has non-specific interactions with its environment (but does not specifically interact with the target entity). The first and the second molecular wires of the device comprise chiral oligonucleotide multiplexes having identical nucleobase sequences and opposite absolute configuration.

The chiral oligonucleotide multiplex of the first molecular wire comprises one strand (a capture strand) that is conjugated to the capture agent and a different (i.e., complementary) strand (a capture surface strand) that is attached to each capture surface. The capture strand and the capture surface strand are complementary and have the same absolute stereochemistry. Likewise, the chiral oligonucleotide multiplex of the second molecular wire comprises one strand (a reference strand) that is conjugated to the reference compound and a different (i.e., complementary) strand (a reference surface strand) that is attached to each reference surface. The reference strand and the reference surface strand are complementary and have the same absolute stereochemistry. The capture strand and the reference strand are enantiomers, and the capture surface strand and the reference surface strand are enantiomers.

The first molecular wire can be attached to its surface(s) (the one or more capture surfaces) by attaching the capture surface strand to the surface(s), and then allowing the capture strand(s) to hybridize with the capture surface strand(s), forming the multiplex of the first molecular wire. Similarly, the second molecular wire can be attached to its surface(s) (the one or more reference surfaces) by attaching the reference surface strand to the surface(s), and then allowing the reference strand(s) to hybridize with the reference surface strand(s), forming the multiplex of the second molecular wire. The capture agent and the reference compound can be conjugated to the capture strand(s) and reference strand(s), respectively, before these strands undergo hybridization. The capture surface strands and the reference surface strands can be attached to their respective surfaces through a functional handle, such as a sulfur-containing compound, as previously described herein. For example, the sulfur-containing compound can be conjugated to the capture surface strand(s) and the reference surface strand(s) to form oligonucleotide conjugates, which are then bonded to the appropriate surfaces via the sulfur functionality of the functional handle. The sulfur-containing compounds conjugated to the capture surface strands and the reference surface strands can be identical and achiral. Alternatively, the sulfur-containing compounds conjugated to the capture surface strands and the reference surface strands can be enantiomers. The sulfur-containing compounds have been previously described herein.

Upon reading this disclosure, those of skill in the art will appreciate, through the principles disclosed herein, alternative structural and functional designs within the scope of the claimed invention. Thus, while particular implementations and applications have been illustrated and described, it is to be understood that the disclosed implementations are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

The following terms and phrases, as used in this disclosure, have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the term "physiological environment" refers to the environmental contents (e.g., plasma, cells, etc.) and/or conditions (e.g., temperature, pH, etc.) in the body.

As used herein, the term "attach," "attached," or "attachment" refers to connecting or uniting by a chemical bond, link, or force in order to keep two or more components together.

As used herein, "polymer" indicates a large molecule comprised of repeating structural units ("-mers") typically connected by covalent chemical bonds.

As used herein, the singular forms "a," "an," and "the" include plural referents unless the context clearly dictates otherwise. For example, reference to "a substituent" encompasses a single substituent as well as two or more substituents, and the like.

As used herein, the term "about," when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

As used herein, "for example," "for instance," "such as," and "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

What is claimed is:

1. A system for sensing a biological or chemical entity, comprising:
    a primary surface;
    first and second conductive surfaces disposed on the primary surface;
    a first molecular wire electrically coupling the first conductive surface to a capture agent that can interact with the biological or chemical entity; and
    a second molecular wire electrically coupling the second conductive surface to a reference compound,
    wherein the first and the second molecular wires comprise chiral oligonucleotide multiplexes having identical nucleobase sequences and opposite absolute configuration.

2. The system of claim 1, wherein the chiral oligonucleotide multiplexes are triplexes or quadruplexes.

3. The system of claim 1, wherein the chiral oligonucleotide multiplexes are duplexes.

4. The system of claim 3, wherein the duplexes are selected from the group consisting of a DNA-DNA homoduplex, a RNA-RNA homoduplex, a PNA-PNA homoduplex, a PMO-PMO homoduplex, a DNA-RNA heteroduplex, a DNA-PNA heteroduplex, a DNA-PMO heteroduplex, a RNA-PNA heteroduplex, and a PNA-PMO heteroduplex.

5. The system of claim 4, wherein the duplex is selected from the group consisting of a DNA-DNA homoduplex, a PNA-PNA homoduplex, and a DNA-PNA heteroduplex.

6. The system of claim 3, wherein the duplexes comprise a DNA-DNA homoduplex.

7. The system of claim 1, wherein a multiplex of the first molecular wire comprises one strand that is coupled to the capture agent and a complementary strand that is coupled to the first conductive surface; and a multiplex of the second molecular wire comprises one strand that is coupled to the reference compound and a complementary strand that is coupled to the second conductive surface.

8. The system of claim 1, wherein the chiral oligonucleotide multiplexes comprise deoxyribonucleic acid (DNA), ribonucleic acid (RNA), peptide nucleic acid (PNA), phosphorodiamidate morpholino oligomer (PMO), or any combination thereof.

9. The system of claim 1, wherein the first molecular wire is electrically coupled to the first conductive surface via a first functional handle comprising a sulfur-containing compound that is covalently bonded to the first molecular wire; and the second molecular wire is electrically coupled to the second conductive surface via a second functional handle comprising a sulfur-containing compound that is covalently bonded to the second molecular wire.

10. The system of claim 9, wherein the first and the second functional handles are achiral and identical.

11. The system of claim 9, wherein the first and the second functional handles are enantiomers.

12. The system of claim 9, wherein the first and the second functional handles are (i) achiral and identical or (ii) enantiomers, and wherein the first and the second functional handles comprise sulfur-containing heterocycles that datively bond to the first and the second conductive surfaces.

13. The system of claim 9, wherein the first and the second functional handles are achiral and identical, and comprise sulfur-containing heterocycles that datively bond to the first and the second conductive surfaces.

14. The system of claim 13, wherein the sulfur-containing heterocycles comprise thiophene or a derivative thereof, or benzothiophene or a derivative thereof.

15. The system of claim 13, wherein the sulfur-containing heterocycles comprise thiahelicene or a derivative thereof.

16. The system of claim 1, wherein the capture agent and the reference compound are each individually an organic compound having a molecular weight less than 900 daltons, a peptide, a protein, a carbohydrate, a lipid, or an oligonucleotide.

17. The system of claim 16, wherein the capture agent and the reference compound are each individually a protein, and wherein the protein is an antibody, an antibody fragment, or an aptamer.

18. The system of claim 1, further comprising differential amplifier circuitry, wherein the first and second conductive surfaces are first and second pads, respectively, disposed on the primary surface and electrically coupled to respective inputs of the differential amplifier circuitry.

19. The system of claim 18, further comprising logic circuitry electrically coupled to an output of the differential amplifier circuitry.

20. The system of claim 19, wherein:
the logic circuitry includes a latch; and
the output of the differential amplifier circuitry triggers the latch when the output exceeds a threshold voltage.

21. The system of claim 19, further comprising an effector mechanism, wherein the logic circuitry is configured to activate the effector mechanism.

22. The system of claim 21, wherein the effector mechanism includes a nano-needle and nano-needle driving circuitry.

23. The system of claim 21, wherein the effector mechanism includes a therapeutic release module.

24. The system of claim 19, wherein the system is a nanoscale or microscale device with a non-conductive housing, and wherein the non-conductive housing includes the primary surface.

25. The system of claim 24, wherein the logic circuitry is manufactured using a 10 nanometer or smaller transistor node.

26. The system of claim 24, wherein the non-conductive housing has a major axis length between 100 nanometers and 500 microns.

27. The system of claim 19, wherein the system is a microscale device with a non-conductive housing, and wherein the non-conductive housing includes the primary surface.

28. The system of claim 27, further comprising:
energy harvesting circuitry configured to provide power to at least the differential amplifier circuitry; and
a first set of one or more antennas supported by the non-conductive housing and electrically coupled to the energy harvesting circuitry.

29. The system of claim 28, wherein each antenna of the first set of one or more antennas comprises a multi-turn or multilayer coil.

30. The system of claim 28, further comprising signaling circuitry, wherein the signaling circuitry is (i) electrically coupled to the logic circuitry and either the first set of one or more antennas or a second set of one or more antennas and (ii) configured to communicate with an external transmitter or receiver via either the first set of one or more antennas or the second set of one or more antennas.

31. The system of claim 30, wherein the signaling circuitry is (i) electrically coupled to the logic circuitry and the first set of one or more antennas and (ii) configured to communicate with the external transmitter or receiver via the first set of one or more antennas.

32. The system of claim 1, wherein the first and second molecular wires each have a length no less than 0.3 nanometers and no more than 10 nanometers.

33. The system of claim 1, wherein the first and second conductive surfaces each have a major axis or diameter that is no less than 2 nanometers.

34. The system of claim 33, wherein the first and second conductive surfaces each have a major axis or diameter that is no less than 10 nanometers.

35. The system of claim 1, wherein the first and second conductive surfaces are spaced apart by about 50 nanometers.

36. The system of claim 1, wherein the system is for sensing biological entities in a physiological environment, and wherein the first and second molecular wires are no more than 2 nanometers distant from the first and second conductive surfaces, respectively.

37. The system of claim 1, wherein the chiral oligonucleotide multiplexes comprise deoxyribonucleic acid (DNA).

* * * * *